US009375171B2

(12) United States Patent
Teixeira

(10) Patent No.: US 9,375,171 B2
(45) Date of Patent: Jun. 28, 2016

(54) PROBABILISTIC BIOMEDICAL PARAMETER ESTIMATION APPARATUS AND METHOD OF OPERATION THEREFOR

(76) Inventor: Rodrigo E. Teixeira, Madison, AL (US)

( * ) Notice: Subject to any disclaimer, the term of this patent is extended or adjusted under 35 U.S.C. 154(b) by 277 days.

(21) Appl. No.: 13/096,876

(22) Filed: Apr. 28, 2011

(65) Prior Publication Data
US 2012/0277545 A1 Nov. 1, 2012

Related U.S. Application Data

(63) Continuation-in-part of application No. 12/796,512, filed on Jun. 8, 2010, now Pat. No. 9,060,722, which is a continuation-in-part of application No. 12/640,278, filed on Dec. 17, 2009.

(60) Provisional application No. 61/171,802, filed on Apr. 22, 2009, provisional application No. 61/366,437, filed on Jul. 21, 2010, provisional application No. 61/372,190, filed on Aug. 10, 2010, provisional application No. 61/373,809, filed on Aug. 14, 2010.

(51) Int. Cl.
A61B 5/00 (2006.01)
A61B 5/1455 (2006.01)
A61B 5/0205 (2006.01)

(52) U.S. Cl.
CPC ........... A61B 5/14551 (2013.01); A61B 5/0075 (2013.01); A61B 5/0205 (2013.01); A61B 5/441 (2013.01); A61B 5/7275 (2013.01)

(58) Field of Classification Search
USPC ....................................... 600/301
See application file for complete search history.

(56) References Cited

U.S. PATENT DOCUMENTS

| 4,802,486 A | 2/1989 | Goodman et al. |
| 5,626,140 A | 5/1997 | Feldman et al. |
| 5,853,364 A | 12/1998 | Baker |
| 6,405,108 B1 | 6/2002 | Patel |
| 6,463,311 B1 | 10/2002 | Diab |

(Continued)

FOREIGN PATENT DOCUMENTS

WO  WO 2008/055173 A2  5/2008

OTHER PUBLICATIONS

Rutledge, G., "Dynamic Selection of Models," 1995.*

(Continued)

Primary Examiner — Michael Kahelin
Assistant Examiner — Mitchell E Alter
(74) Attorney, Agent, or Firm — Kevin Hazen

(57) ABSTRACT

A probabilistic digital signal processor for medical function is described. Initial probability distribution functions are input to a dynamic state-space model, which operates on state and/or model probability distribution functions to generate a prior probability distribution function, which is input to a probabilistic updater. The probabilistic updater integrates sensor data with the prior to generate a posterior probability distribution function passed to a probabilistic sampler, which estimates one or more parameters using the posterior, which is output or re-sampled in an iterative algorithm. For example, the probabilistic processor operates using a physical model on data from a medical meter, where the medical meter uses a first physical parameter, such as blood oxygen saturation levels from a pulse oximeter, to generate a second physical parameter not output by the medical meter, such as a heart stroke volume, a cardiac output flow rate, and/or a blood pressure.

19 Claims, 18 Drawing Sheets

(56) References Cited

U.S. PATENT DOCUMENTS

| | | | |
|---|---|---|---|
| 6,505,145 | B1 | 1/2003 | Bjornson |
| 6,511,436 | B1 | 1/2003 | Asmar |
| 6,728,660 | B2 | 4/2004 | Bjornson |
| 6,882,959 | B2 | 4/2005 | Rui |
| 7,006,947 | B2 | 2/2006 | Tryon |
| 7,016,825 | B1 | 3/2006 | Tryon |
| 7,018,338 | B2 | 3/2006 | Vetter et al. |
| 7,020,507 | B2 | 3/2006 | Scharf |
| 7,027,953 | B2 | 4/2006 | Klein |
| 7,058,550 | B2 | 6/2006 | Kouritzin |
| 7,079,888 | B2 | 7/2006 | Oung et al. |
| 7,149,320 | B2 | 12/2006 | Haykin |
| 7,191,110 | B1 | 3/2007 | Charbel |
| 7,260,501 | B2 | 8/2007 | Pattipatti |
| 7,289,906 | B2 | 10/2007 | Merwe |
| 7,317,770 | B2 | 1/2008 | Wang |
| 7,460,915 | B2 | 12/2008 | Marik et al. |
| 7,480,601 | B2 | 1/2009 | Tryon |
| 7,536,277 | B2 | 5/2009 | Pattipatti |
| 8,494,829 | B2 | 7/2013 | Teixeira |
| 2004/0122703 | A1 | 6/2004 | Walker et al. |
| 2004/0171950 | A1* | 9/2004 | Starr et al. ................ 600/508 |
| 2005/0113703 | A1 | 5/2005 | Farringdon et al. |
| 2005/0143634 | A1 | 6/2005 | Baker et al. |
| 2006/0166176 | A1 | 7/2006 | Lakin |
| 2006/0190217 | A1 | 8/2006 | Lee |
| 2007/0100213 | A1 | 5/2007 | Dossas et al. |
| 2008/0027341 | A1 | 1/2008 | Sackner |
| 2008/0082018 | A1 | 4/2008 | Sackner et al. |
| 2009/0024332 | A1 | 1/2009 | Karlov |
| 2009/0069647 | A1 | 3/2009 | McNames |
| 2010/0228102 | A1* | 9/2010 | Addison et al. ............ 600/301 |
| 2010/0274102 | A1* | 10/2010 | Teixeira .................... 600/301 |
| 2011/0077484 | A1 | 3/2011 | Van Slyke et al. |
| 2011/0301436 | A1 | 12/2011 | Teixeira |
| 2012/0022336 | A1 | 1/2012 | Teixeira |
| 2012/0022350 | A1 | 1/2012 | Teixeira |
| 2012/0022384 | A1 | 1/2012 | Teixeira |
| 2012/0022805 | A1 | 1/2012 | Teixeira |
| 2012/0022844 | A1 | 1/2012 | Teixeira |
| 2012/0277545 | A1 | 11/2012 | Teixeira |
| 2014/0275886 | A1 | 9/2014 | Teixeira |

OTHER PUBLICATIONS

Lendek, Zs, et al., "State Estimation Under Uncertainty: A Survey," 2006.*

Saatci, E. et al., "Dual Unscented Kalman Filter and Its Applications to Respiratory System Modelling," Source: Kalman Filter: Recent Advances and Applications, Book edited by: Victor M. Moreno and Alberto Pigazo,, pp. 584, Apr. 2009, I-Tech, Vienna, Austria.*

Merwe, "Sigma-Point Kalman Filters for Probabilistic Inference in Dynamic State-Space Models", Apr. 2004, pp. 1-397, Oregon Health and Science University, Oregon.*

"Monitoring Metabolic Status: Predicting Decrements in Physiological and Cognitive Performance During Military", Apr. 2004, pp. 1-4, Report Brief, Institute of Medicine of the National Academies.

"Monitoring Metabolic Status: Predicting Decrements in Physiological and Cognitive Performance", 2004, pp. 1-33, Committee on Metabolic Monitoring for Military Field Applications, Standing Committee on Military Nutrition Research.

Arulampalam, Maskell, and Clapp, "A Tutorial on Particle Filters for Online Nonlinear/Non-Gaussian Bayesian Tracking", Feb. 2002, pp. 1-15, vol. 50, No. 2, IEEE Transactions on Signal Processing.

Bashi, Jiikov, Li, and Chen, "Distributed Implementations of Particle Filters", pp. 1-8.USA.

Boers and Driessen, "Particle Filter Track Before Detect Algorithms" Mar. 12, 2003, pp. 1-23, Thales.

Bokareva, Hu, Kanhere, Ristic, Gordon, Bessell, Rutten, and Jha, "Wireless Sensor Networks for Battlefield Surveillance", Oct. 2006, pp. 1-8, Land Warfare Conference.

Briegel and Tresp, "A Nonlinear State Space Model for the Blood Glucose Metabolism of a Diabetic", May 2002, pp. 228-236, Anwendungsaufsatz.

Chen, "Bayesian Filtering: From Kalman Filters to Particle Filters and Beyond", pp. 1-69.

Chen, Bakshi, Goel, and Ungarala, "Bayesian Estimation via Sequential Mote Carlo Sampling—Unconstrained Nonlinear Dynamic Systems", pp. 1-39.

Chen, Lee, Budhiraja, and Mehra, "PFLib—An Object Oriented MATLAB Toolbox for Particle Filtering", pp. 1-8.

Clifford and McSharry, "A Realistic Coupled Nonlinear Artificial ECG, BP, and Respiratory Signal Generator for Assessing Noise Performance of Biomedical Signal Processing Algorithms", pp. 1-12.

Clifford, "A Novel Framework for Signal Representation and Source Separation; Applications to Filtering and Segmentation of Biosignals", May 17, 2006. pp. 1-15. WSPC/Instruction File, Massachusetts, USA.

Clifford, Shoeb, Mcsharry, and Janz, "Model-Based Filtering, Compression and Classification of the ECG", pp. 1-4.

Crisan and Doucet, "A Survey of Convergence Results on Particle Filtering Methods for Practitioners", Mar. 2002, pp. 1-11, vol. 50, No. 3, IEEE Transactions on Signal Processing.

Dawant, Uckun, Manders, and Lindstrom, "Model-Based Signal Acquisition, Analysis, and Interpretation in Intelligent Patient Monitoring", Dec. 1993, pp. 82-92, IEEE Engineering in Medicine and Biology.

Doucet, Freitas, Murphy, and Russell, "Rao-Blackwellised Particle Filtering for Dynamic Bayesian Networks", pp. 1-8.

Dripps, "An Introduction to Model Based Digital Signal Processing", pp. 1-4.

Feuerstein, Parker, and Bouotelle, "Practical Methods for Noise Removal: Applications to Spikes, Nonstationary Quasi-Periodic Noise, and Baseline Drift", May 18, 2009, pp. 1-20, American Chemical Society.

Ford, "Non-Linear and Robust Filtering: From the Kalman Filter to the Particle Filter", Apr. 2002, pp. 1-53, DSTO Aeronautical I and Maritime Research Laboratory, Australia.

Goebel, "Pronostics", Apr. 27, 2010, pp. 1-47, NASA Ames Research Center, Moffett Field, CA.

Hall and Llinas, "An Introduction to Multisensor Data Fusion", Jan. 1997, pp. 1-18, vol. 85, No. 1, Proceedings of the IEEE.

Han, Kim, and Kim, "Development of Real-Time Motion Artifact Reduction Algorithm for a Wearable Photoplethysmography", pp. 1-4, Aug. 23, 2007, Proceedings of the 29th Annual International Conference of the IEEE EMBS, Lyon, France.

Hoyt, "SPARNET~Spartan Sensor Network to Improve Medical and Situational Awareness of Foot Soldiers During Field Training", Jan. 9, 2007, pp. 1-2, U.S. Army Research Institute of Environmental Medicine. MA.

Hsiao, Plinval-Salgues, and Miller, "Particle Filters and Their Applications", Apr. 11, 2005, pp. 1-99, Cognitive Robotics.

Huang and Wang, "Overview of Emerging Bayesian Approach to Nonlinear System Identification", Apr. 6, 2006, pp. 1-12, International Workshop on Solving Industrial Control and Optimization Problems, Cramado, Brazil.

Nutter and Dearden, "The Gaussian Particle Filter for Diagnosis of Non-Linear Systems", pp. 1-6, Tecnische Universitat Darmstadt, NASA Ames Research Center. CA.

Isermann, "Model-Based Fault-Detection and Diagnosis—Status and Applications", pp. 71-85, Annual Reviews in Control.

Johansen, Doucet, and Davy, "Particle Methods for Maximum Likelihood Estimation in Latent Variable Models", Aug. 31, 2007, pp. 1-11, Springer.

Kantas, Doucet, Singh, and Maciejowski, "An Overview of Sequential Monte Carlo Methods for Parameter Estimation in General State-Space Models", pp. 1-19.

Kueck and Freitas, "Where Do Priors and Causal Models Come From? An Experimental Design Perspective", Apr. 7, 2010, pp. 1-13, University of British Columbia, Technical Report.

Lee, "A Particle Algorithm for Sequential Bayesian Parameter Estimation and Model Selection", Feb. 2, 2002. pp. 1-11, vol. 50, No. 2, IEEE Transactions on Signal Processing.

Maybeck, "Stochastic Models, Estimation, and Control", pp. 1-19, vol. 1, Academic Press.

(56) References Cited

OTHER PUBLICATIONS

McSharry and Clifford, "Open-Source Software for Generating Electrocardiogram Signals", Jun. 4, 2004, pp. 1-10, Psys.Med.Biol.
Merwe and Wan, "Gaussian Mixture Sigma-Point Particle Filters for Sequential Probabilistic Inference in Dynamic State-Space Models", pp. 1-4.
Merwe and Wan, "Sigma-Point Kalman Filters for Probabilistic Inference in Dynamic State-Space Models", pp. 1-27, OGI School of Science and Engineering, Oregon Health and Science University, Oregon, USA.
Merwe and Wan, "The Square-Root Unscented Kalman Filter for State and Parameter-Estimation" pp. 1-4, Oregon Graduate Institute of Science and Technology. Oregon, USA.
Merwe, "Sigma-Point Kalman Filters for Probabilistic Inference in Dynamic State-Space Models", Apr. 2004, pp. 1-397, Oregon Health and Science University. Oregon.
Merwe, Doucet, Freitas, and Wan, "The Unscented Particle Filter", Aug. 16, 2000, pp. 1-46, Cambridge University Engineering Department, Technical Report.
Merwe, Julier, and Wan, "Sigma-Point Kalman Filters for Nonlinear Estimation and Sensor-Fusion-Application to Integrated Navigation", pp. 1-30, American Institute of Aeronautics and Astronautics.
Morales-Menendez, Freitas, and Poole, "Real-Time Monitoring of Complex Industrial Processes with Particle Filters", pp. 1-8.
Niethammer, "Introduction to Estimation Theory", pp. 1-49, Department of Computer Science University of North Carolina.
Norris, Suwanmongkol, Geissbuhler, and Dawant, "The SIMON Architecture: Distributing Data, Tasks, and Knowledge in Intelligent ICU Monitoring Systems", pp. 1-10, Vanderbilt University, Tennessee.
Oreshkin and Coates, "Bootstrapping Particle Filters using Kernel Recursive Least Squares", pp. 1-7, Department of Electrical and Computer Engineering, Canada.
Parker, "A Model-Based Algorithm for Blood Glucose Control in Type I Diabetic Patients", Feb. 1999, pp. 1-10, vol. 46, No. 2, IEEE Transactions on Biomedical Engineering.
Rasmussen and Ghahramani, "Bayesian Monte Carlo", pp. 1-8, Gatsby Computational Neuroscience Unit, London, England.
Sameni, "A Nonlinear Bayesian Filtering Framework for ECG Denoising", vol. XX, No. YY, pp. 1-14, IEEE Transactions on Biomedical Engineering.
Sameni, "A Nonlinear Bayesian Filtering Framework for the Filtering of Noisy ECG Signals", Apr. 21, 2006, pp. 1-62, Laboratoire des Images et des Signaux, France.
Sameni, Shamsollahi, and Jutten, Muti-Channel Electrocardiogram Denoising Using a Bayesian Filtering Framework, 2006. pp. 1-4, Computer in Cardiology.
Sameni, Shamsollahi, Jutten, and Zadeh, "Filtering Noisy ECG Signals Using the Extended Kalman Filter Based on a Modified Dynamic ECG Model" pp. 1-4.
Storvik, "Particle Filters for State-Space Models With the Presence of Unknown Static Parameters", Feb. 2002, pp. 281-289, vol. 50, No. 2, IEEE Transactions on Signal Processing.
Thrun, "Particle Filters in Robotics or: How the World Became to Be One Big Bayes Network" Aug. 2, 2002, pp. 1-74, UAI.
Thrun, "Stanley: The Robot That Won the DARPA Grand Challenge", pp. 1-41, Stanford Artificial Intelligence Laboratory, CA.
Verma, Thrun, and Simmons, "Variable Resolution Particle Filter", Aug. 2003, pp. 1-6, in Proceedings of the International Joint Conference on Artificial Intelligence.
Wan, Merwe, and Nelson, "Dual Estimation and the Unscented Transformation", pp. 1-7, Oregon Graduate Institute of Science and Technology Department of Electrical and Computer Engineering, Portland, Oregon.
Wegman, Leuenberger, Neuenschwander, and Excoffier, "ABCtoolbox: A Versatile toolkit for Approximate Bayesian Computations", Mar. 4, 2010, BMC Bioinformatics.
Welch and Biship, "An Introduction to the Kalman Filter", Jul. 24, 2006, pp. 1-16, Department of Computer Science University of North Carolina, NC.
Welch and Bishop, "An Introduction to the Kalman Filter", pp. 1-80. Association for Computing Machinery.
Welch, "Team18: The Kalman Filter Learning Tool Dynamic and Measurement Models", Feb. 17, 2003, pp. 1-11, University of North Carolina. NC.
Wu, Rangaraj, Rangayyan, and Ng, "Cancellation of Artifacts in ECG Signals Using a Normalized Adaptive Neural Filter", pp. 1-4, Aug. 23, 2007, Proceedings of the 29$^{th}$ Annual International Conference of the IEEE EMBS, Lyon, France.
Xu and Li, "Rao-Blackwellised Particle Filter for Tracking with Application in Visual Surveillance", pp. 1-8, Department of Computer Science and Engineering Arizona State University, AZ.
Arulampalam et al. IEEE Transactions on Signal Processing, vol. 50, No. 2, 2002, 174-187.
Singer et al. Pub Med PMID:3063772, abstract ( J Electrocardiol. 1988;21 Suppl:S46-S55).
Wukitsch et al., Journal of Clinical Monitoring, vol. 4, pp. 290-301, 1998.
Merwe, "Sigma-Point Kalman Filters for Probabilistic Inference in Dynamic State-Space Models", Apr. 2004, pp. 1-379, Oregon Health and Science University, Oregon.
Saatci, E. et al., Dual Unscented Kalman Filter and Its Applications to Respiratory System Modelling,: Source: Kalman Filter: Recent Advances and Applications, Book edited by: Victor M. Moreno and Alberto Pigazo,, pp. 584, Apr. 2009, I-Tech, Vienna, Austria.

* cited by examiner

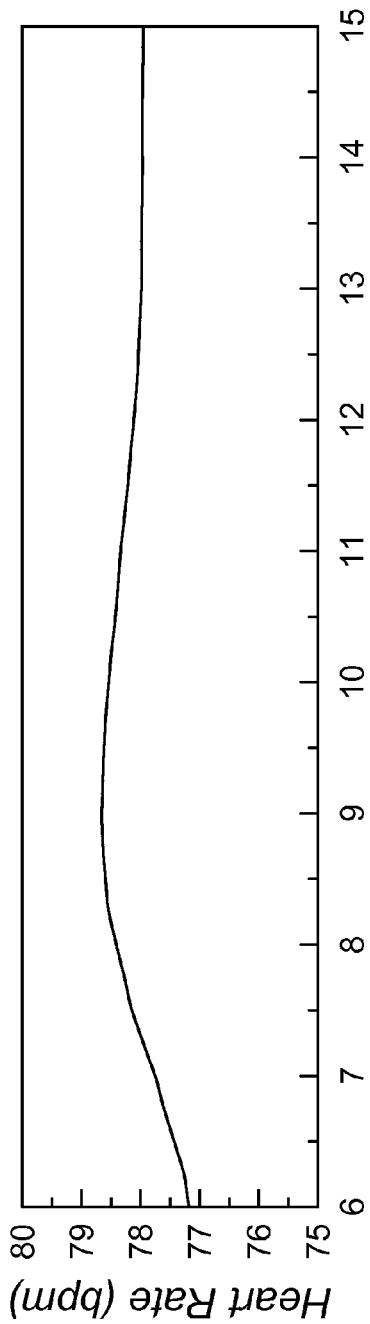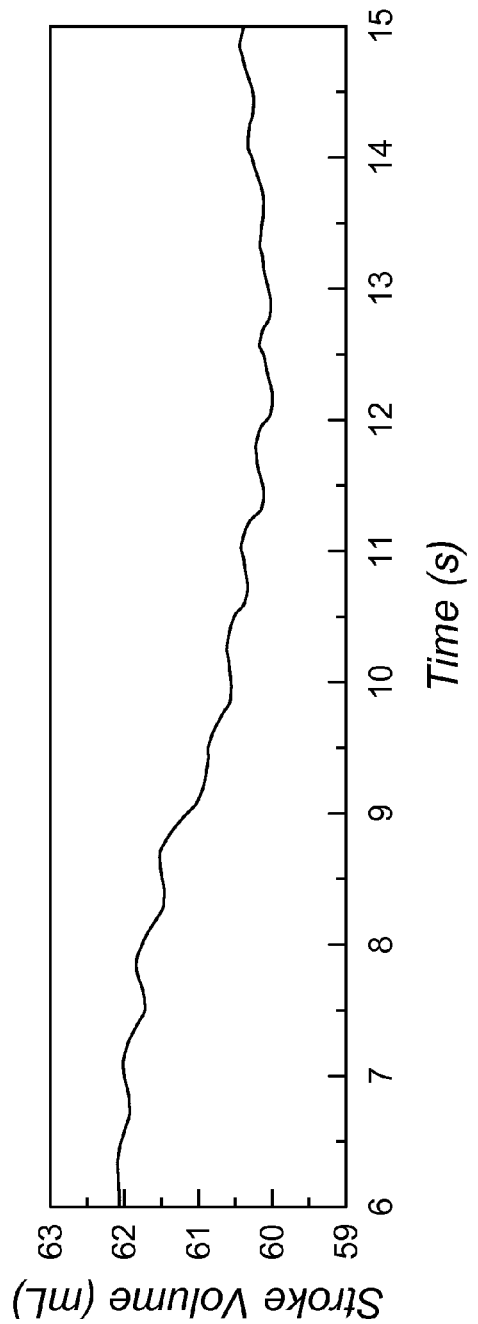
FIG. 9B
FIG. 9C

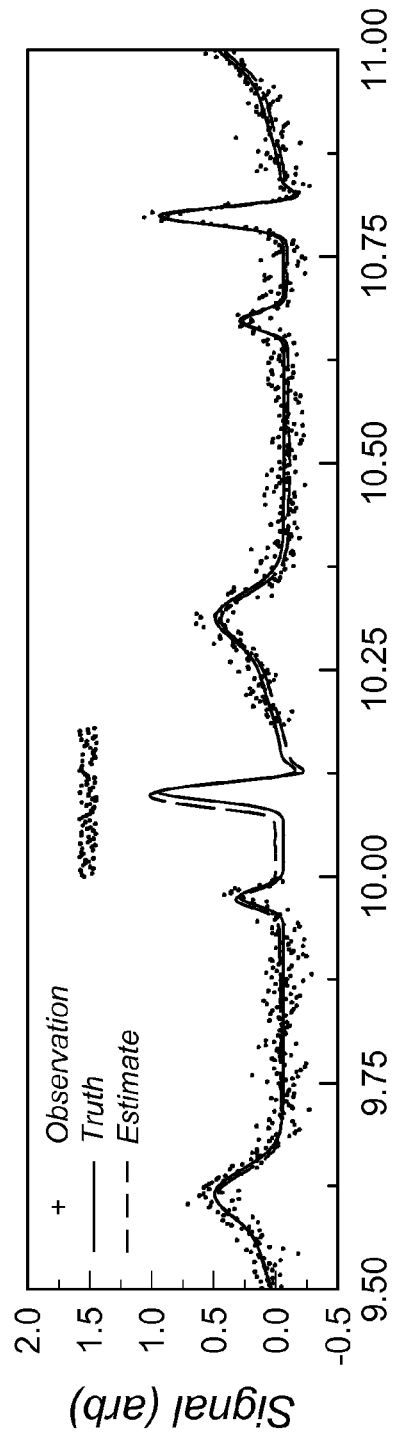
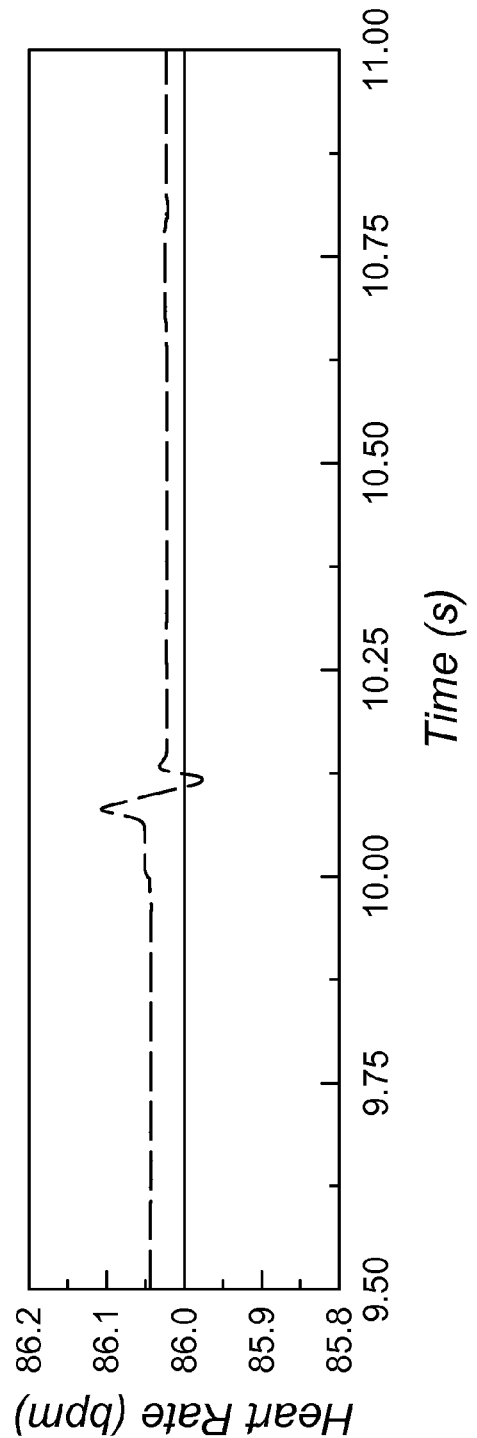
FIG. 13A
FIG. 13B

PROBABILISTIC BIOMEDICAL PARAMETER ESTIMATION APPARATUS AND METHOD OF OPERATION THEREFOR

CROSS-REFERENCES TO RELATED APPLICATIONS

This application claims:
priority to U.S. patent application Ser. No. 12/796,512, filed Jun. 8, 2010, which claims priority to U.S. patent application Ser. No. 12/640,278, filed Dec. 17, 2009, which under 35 U.S.C. 120 claims benefit of U.S. provisional patent application No. 61/171,802, filed Apr. 22, 2009,
benefit of U.S. provisional patent application No. 61/366,437 filed Jul. 21, 2010;
benefit of U.S. provisional patent application No. 61/372,190 filed Aug. 10, 2010; and
benefit of U.S. provisional patent application No. 61/373,809 filed Aug. 14, 2010,
all of which are incorporated herein in their entirety by this reference thereto.

STATEMENT REGARDING FEDERALLY SPONSORED RESEARCH OR DEVELOPMENT

The U.S. Government may have certain rights to this invention pursuant to Contract Number IIP-0839734 awarded by the National Science Foundation.

BACKGROUND OF THE INVENTION

1. Field of the Invention

The present invention relates generally to apparatus and methods for processing and/or representing physiological sensor data.

2. Discussion of the Related Art

Biomedical monitoring devices such as pulse oximeters, glucose sensors, electrocardiograms, capnometers, fetal monitors, electromyograms, electroencephalograms, and ultrasounds are sensitive to noise and artifacts. Typical sources of noise and artifacts include baseline wander, electrode-motion artifacts, physiological artifacts, high-frequency noise, and external interference. Some artifacts can resemble real processes, such as ectopic beats, and cannot be removed reliably by simple filters; however, these are removable by the techniques taught herein.

Patents related to the current invention are summarized herein.

Mechanical Systems

Several reports of diagnostics and prognostics applied to mechanical systems have been reported.

Vibrational Analysis

R. Klein "Method and System for Diagnostics and Prognostics of a Mechanical System", U.S. Pat. No. 7,027,953 B2 (Apr. 11, 2006) describes a vibrational analysis system for diagnosis of health of a mechanical system by reference to vibration signature data from multiple domains, which aggregates several features applicable to a desired fault for trend analysis of the health of the mechanical system.

Intelligent System

S. Patel, et. al. "Process and System for Developing Predictive Diagnostic Algorithms in a Machine", U.S. Pat. No. 6,405,108 B1 (Jun. 11, 2002) describe a process for developing an algorithm for predicting failures in a system, such as a locomotive, comprising conducting a failure mode analysis to identify a subsystem, collecting expert data on the subsystem, and generating a predicting signal for identifying failure modes, where the system uses external variables that affect the predictive accuracy of the system.

C. Bjornson, "Apparatus and Method for Monitoring and Maintaining Plant Equipment", U.S. Pat. No. 6,505,145 B1 (Jan. 11, 2003) describes a computer system that implements a process for gathering, synthesizing, and analyzing data related to a pump and/or a seal, in which data are gathered, the data is synthesized and analyzed, a root cause is determined, and the system suggests a corrective action.

C. Bjornson, "Apparatus and Method for Monitoring and Maintaining Plant Equipment", U.S. Pat. No. 6,728,660 B2 (Apr. 27, 2004) describes a computer system that implements a process for gathering, synthesizing, and analyzing data related to a pump and/or a seal, in which data are gathered, the data is synthesized and analyzed, and a root cause is determined to allow a non-specialist to properly identify and diagnose a failure associated with a mechanical seal and pump.

K. Pattipatti, et. al. "Intelligent Model-Based Diagnostics for System Monitoring, Diagnosis and Maintenance", U.S. Pat. No. 7,536,277 B2 (May 19, 2009) and K. Pattipatti, et. al. "Intelligent Model-Based Diagnostics for System Monitoring, Diagnosis and Maintenance", U.S. Pat. No. 7,260,501 B2 (Aug. 21, 2007) both describe systems and methods for monitoring, diagnosing, and for condition-based maintenance of a mechanical system, where model-based diagnostic methodologies combine or integrate analytical models and graph-based dependency models to enhance diagnostic performance.

Inferred Data

R. Tryon, et. al. "Method and Apparatus for Predicting Failure in a System", U.S. Pat. No. 7,006,947 B2 (Feb. 28, 2006) describe a method and apparatus for predicting system failure or reliability using a computer implemented model relying on probabilistic analysis, where the model uses data obtained from references and data inferred from acquired data. More specifically, the method and apparatus uses a pre-selected probabilistic model operating on a specific load to the system while the system is under operation.

Virtual Prototyping

R. Tryon, et. al. "Method and Apparatus for Predicting Failure of a Component", U.S. Pat. No. 7,016,825 B1 (Mar. 21, 2006) describe a method and apparatus for predicting component failure using a probabilistic model of a material's microstructural-based response to fatigue using virtual prototyping, where the virtual prototyping simulates grain size, grain orientation, and micro-applied stress in fatigue of the component.

R. Tryon, et. al. "Method and Apparatus for Predicting Failure of a Component, and for Determining a Grain Orientation Factor for a Material", U.S. Pat. No. 7,480,601 B2 (Jan. 20, 2009) describe a method and apparatus for predicting component failure using a probabilistic model of a material's microstructural-based response to fatigue using a computer simulation of multiple incarnations of real material behavior or virtual prototyping.

Medical Systems

Several reports of systems applied to biomedical systems have been reported.

Lung Volume

M. Sackner, et. al. "Systems and Methods for Respiratory Event Detection", U.S. patent application no. 2008/0082018 A1 (Apr. 3, 2008) describe a system and method of processing respiratory signals from inductive plethysmographic sensors in an ambulatory setting that filters for artifact rejection to improve calibration of sensor data and to produce output indicative of lung volume.

Pulse Oximeter

J. Scharf, et. al. "Separating Motion from Cardiac Signals Using Second Order Derivative of the Photo-Plethysmograph and Fast Fourier Transforms", U.S. Pat. No. 7,020,507 B2 (Mar. 28, 2006) describes the use of filtering photo-plethysmograph data in the time domain to remove motion artifacts.

M. Diab, et. al. "Plethysmograph Pulse Recognition Processor", U.S. Pat. No. 6,463,311 B1 (Oct. 8, 2002) describe an intelligent, rule-based processor for recognition of individual pulses in a pulse oximeter-derived photo-plethysmograph waveform operating using a first phase to detect candidate pulses and a second phase applying a plethysmograph model to the candidate pulses resulting in period and signal strength of each pulse along with pulse density.

C. Baker, et. al. "Method and Apparatus for Estimating Physiological Parameters Using Model-Based Adaptive Filtering", U.S. Pat. No. 5,853,364 (Dec. 29, 1998) describe a method and apparatus for processing pulse oximeter data taking into account physical limitations using mathematical models to estimate physiological parameters.

Cardiac

J. McNames, et. al. "Method, System, and Apparatus for Cardiovascular Signal Analysis, Modeling, and Monitoring", U.S. patent application publication no. 2009/0069647 A1 (Mar. 12, 2009) describe a method and apparatus to monitor arterial blood pressure, pulse oximetry, and intracranial pressure to yield heart rate, respiratory rate, and pulse pressure variation using a statistical state-space model of cardiovascular signals and a generalized Kalman filter to simultaneously estimate and track the cardiovascular parameters of interest.

M. Sackner, et. al. "Method and System for Extracting Cardiac Parameters from Plethysmograph Signals", U.S. patent application publication no. 2008/0027341 A1 (Jan. 31, 2008) describe a method and system for extracting cardiac parameters from ambulatory plethysmographic signal to determine ventricular wall motion.

Hemorrhage

P. Cox, et. al. "Methods and Systems for Non-Invasive Internal Hemorrhage Detection", International Publication no. WO 2008/055173 A2 (May 8, 2008) describe a method and system for detecting internal hemorrhaging using a probabilistic network operating on data from an electrocardiogram, a photoplethysmogram, and oxygen, respiratory, skin temperature, and blood pressure measurements to determine if the person has internal hemorrhaging.

Disease Detection

V. Karlov, et. al. "Diagnosing Inapparent Diseases From Common Clinical Tests Using Bayesian Analysis", U.S. patent application publication no. 2009/0024332 A1 (Jan. 22, 2009) describe a system and method of diagnosing or screening for diseases using a Bayesian probability estimation technique on a database of clinical data.

Statement of the Problem

The influence of multiple sources of contaminating signals often overlaps the frequency of the signal of interest, making it difficult, if not impossible, to apply conventional filtering. Severe artifacts such as occasional signal dropouts due to sensor movement or large periodic artifacts are also difficult to filter in real time. Biological sensor hardware can be equipped with a computer comprising software for post-processing data and reducing or rejecting noise and artifacts. Current filtering techniques typically use some knowledge of the expected frequencies of interest where the sought-after physiological information should be found, and do not contain a mathematical model describing either the physiological processes that are measured or the physical processes that measure the signal.

Adaptive filtering has been used to attenuate artifacts in pulse oximeter signals corrupted with overlapping frequency noise bands by estimating the magnitude of noise caused by patient motion and other artifacts, and canceling its contribution from pulse oximeter signals during patient movement. Such a time correlation method relies on a series of assumptions and approximations to the expected signal, noise, and artifact spectra, which compromises accuracy, reliability, and general applicability.

Biomedical filtering techniques based on Kalman and extended Kalman techniques offer advantages over conventional methods and work well for filtering linear systems or systems with small nonlinearities and Gaussian noise. These filters, however, are not adequate for filtering highly nonlinear systems and non-Gaussian/non-stationary noise. Therefore, obtaining reliable biomedical signals continue to present problems, particularly when measurements are made in mobile, ambulatory, and physically active patients.

Existing data processing techniques, including adaptive noise cancellation filters, are unable to extract information that is hidden or embedded in biomedical signals and also discard some potentially valuable information.

Existing medical sensors sense a narrow spectrum of medical parameters and states. What is needed is a system readily expanding the number of biomedical states determined.

A method or apparatus for extracting additional useful information from a biomedical system, component, or sub-component is needed to provide users and/or health care providers additional and/or clearer biomedical information.

SUMMARY OF THE INVENTION

The invention comprises use of a probabilistic model to extract and/or estimate physiological information from a biomedical sensor.

DESCRIPTION OF THE FIGURES

A more complete understanding of the present invention is derived by referring to the detailed description and claims when considered in connection with the Figures, wherein like reference numbers refer to similar items throughout the Figures.

FIG. 13A and FIG. 13B are charts showing input ECG sensor data and comparing output data from a data processor according to the present invention with output data generating using a Savitzky-Golay FIR data processing algorithm.

DETAILED DESCRIPTION OF THE INVENTION

Figure 1:
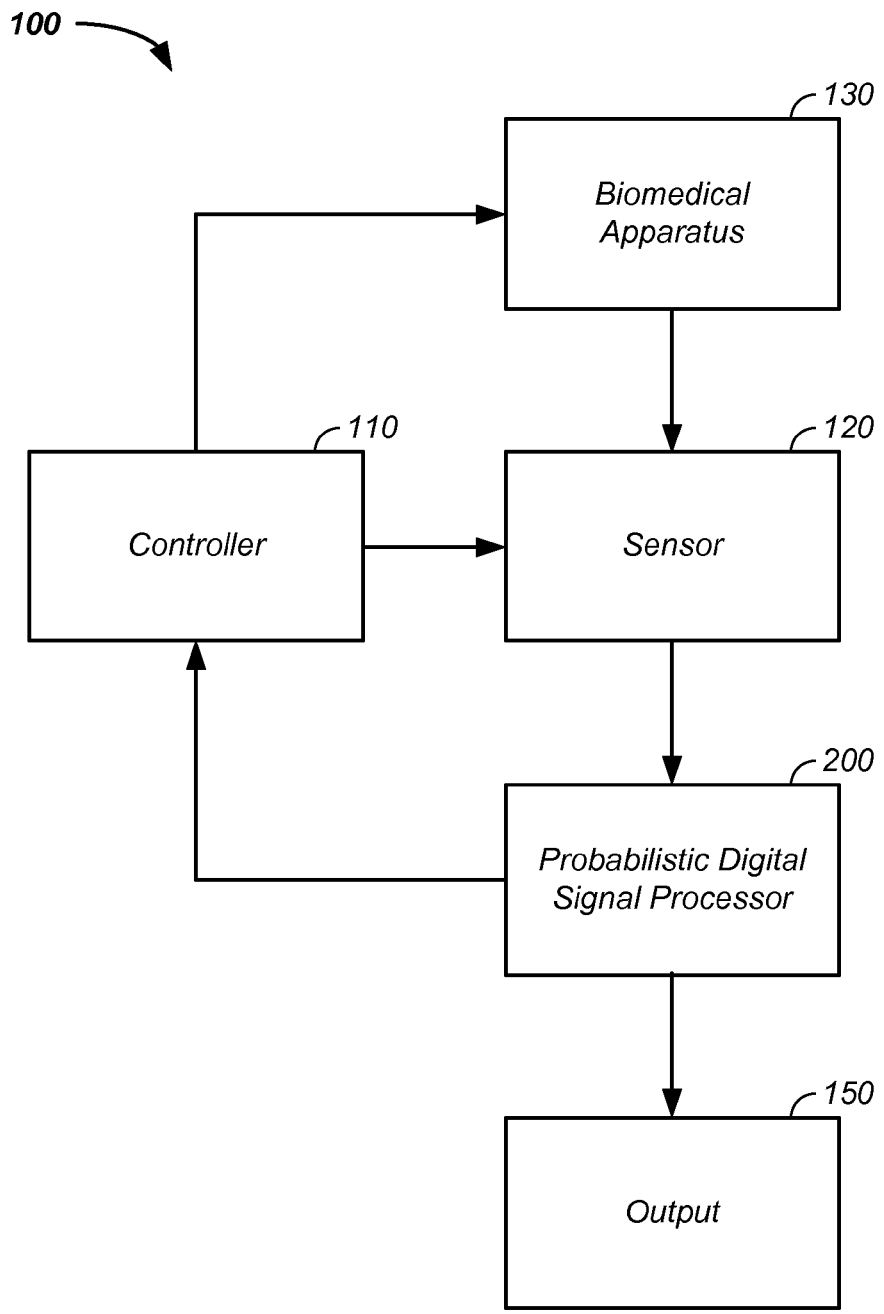
FIG. 1 illustrates operation of an intelligent data extraction algorithm on a biomedical apparatus.

The invention comprises use of a method, a system, and/or an apparatus using a probabilistic model for monitoring and/or estimating a physiological or medical parameter using a biomedical apparatus.

In one embodiment, an intelligent data extraction algorithm (IDEA) is used in a system, which combines a dynamic state-space model with a probabilistic digital signal processor to estimate a parameter, such as a biomedical parameter. Initial probability distribution functions are input to a dynamic state-space model, which iteratively operates on probability distribution functions, such as state and model probability distribution functions, to generate a prior probability distribution function, which is input to a probabilistic updater. The probabilistic updater integrates sensor data with the prior probability distribution function to generate a posterior probability distribution function passed to a probabilistic sampler, which estimates one or more parameters using the posterior, which is output or re-sampled and used as an input to the dynamic state-space model in the iterative algorithm. In various embodiments, the probabilistic data signal processor is used to filter output and/or estimate a value of a new physiological parameter from a biomedical device using appropriate physical models, which optionally include biomedical, chemical, electrical, optical, mechanical, and/or fluid based models. For clarity, examples of heart and cardiovascular medical devices are provided.

In various embodiments, the probabilistic digital signal processor comprises one or more of a dynamic state-space model, a dual or joint updater, and/or a probabilistic sampler, which process input data, such as sensor data and generates an output. Preferably, the probabilistic digital signal processor (1) iteratively processes the data and/or (2) uses a physical model in processing the input data.

The probabilistic digital signal processor optionally:
- operates using data from a medical meter, where the medical meter yields a first physical parameter from raw data, to generate a second physical parameter not output by the medical meter;
- operates on discrete/non-probabilistic input data from a medical device to generate a probabilistic output function;
- iteratively circulates a probability distribution function through at least two of the dynamic state-space model, the dual or joint updater, and/or the probabilistic sampler;
- fuses or combines output from multiple medical devices; and
- prognosticates probability of future events.

To facilitate description of the probabilistic digital signal processor, a non-limiting example of a hemodynamics process model is provided. In this example, the probabilistic digital signal processor is provided:
- raw sensor data, such as current, voltage, and/or resistance; and/or
- output from a medical device to a first physical parameter.

In this example, the medical device is a pulse oximeter and the first physical parameter from the pulse oximeter provided as input to the probabilistic digital signal processor is one or more of:
- raw data;
- heart rate; and/or
- blood oxygen saturation.

The probabilistic digital signal processor uses a physical model, such as a probabilistic model, to operate on the first physical parameter to generate a second physical parameter, where the second physical parameter is not the first physical parameter. For example, the output of the probabilistic digital signal processor when provided with the pulse oximeter data is one or more of:
- a heart stroke volume;
- a cardiac output flow rate;
- an aortic blood pressure; and/or
- a radial blood pressure.

Optionally, the output from the probabilistic model is an updated, error filtered, and/or smoothed version of the original input data, such as a smoothed blood oxygen saturation percentage as a function of time.

Deterministic vs. Probabilistic Models

Typically, computer-based systems use a mapping between observed symptoms of failure and the equipment where the mapping is built using deterministic techniques. The mapping typically takes the form of a look-up table, a symptom-problem matrix, trend analysis, and production rules. In stark contrast, alternatively probabilistic models are used to analyze a system. An example of a probabilistic model, referred to herein as an intelligent data extraction system is provided, infra.

Intelligent Data Extraction System

Referring now to FIG. 1, an algorithm based intelligent data extraction system 100 is illustrated. The intelligent data extraction system 100 uses a controller 110 to control a sensor 120. In one embodiment, the controller 110 comprises a microprocessor in a computer or computer system, an embedded processor, and/or an embedded device. The sensor 120 is used to measure a parameter and/or is incorporated into a biomedical apparatus 130. Optionally, the controller 110 additionally controls the medical apparatus and/or is built into the biomedical apparatus 130. The sensor 120 provides readings to a data processor or a probabilistic digital signal processor 200, which provides feedback to the controller 110 and/or provides output 150. In one embodiment, the controller 110 comprises a microprocessor in a computer or computer system.

Herein, to enhance understanding and for clarity of presentation, non-limiting examples of an intelligent data extraction system operating on a hemodynamics biomedical devices are used to illustrate methods, systems, and apparatus described herein. Generally, the methods, systems, and apparatus described herein extend to any apparatus having a moveable part and/or to any medical device. Examples of the dynamic state-space model with a probabilistic digital signal processor used to estimate parameters of additional biomedical systems are provided after the details of the processing engine are presented.

Still referring to FIG. 1, in a pulse oximeter example the controller 110 controls a sensor 120 in the pulse oximeter apparatus 130. The sensor 120 provides readings, such as a spectral reading to the probabilistic digital signal processor 200, which is preferably a probability based data processor. The probabilistic digital signal processor 200 optionally operates on the input data or provides feedback to the controller 110, such as state of the patient, as part of a loop, iterative loop, time series analysis, and/or generates the output 150, such as a smoothed biomedical state parameter or a new biomedical state parameter. For clarity, the pulse oximeter apparatus is used repetitively herein as an example of the biomedical apparatus 130 upon which the intelligent data extraction system 100 operates. The probabilistic digital signal processor 200 is further described, infra.

Data Processor

Figure 2:
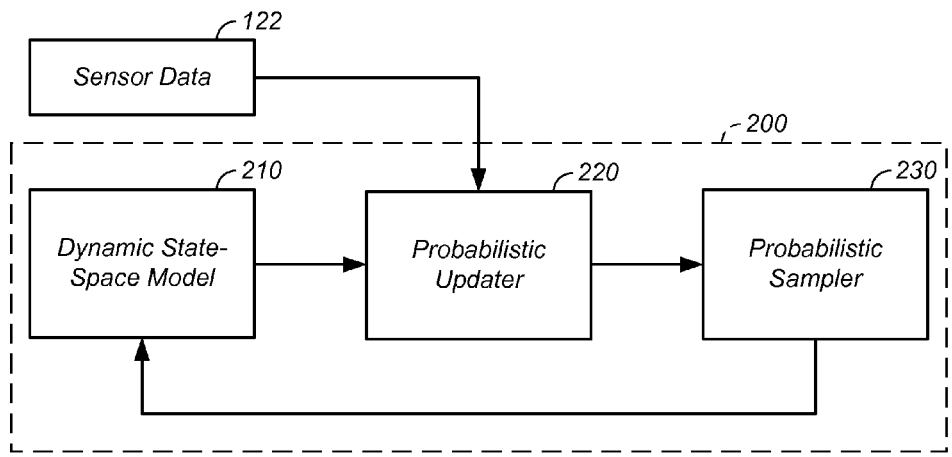
FIG. 2 provides a block diagram of a data processor.

Referring now to FIG. 2, the probabilistic digital signal processor 200 of the intelligent data extraction system 100 is further described. Generally, the data processor includes a dynamic state-space model 210 (DSSM) and a probabilistic updater 220 that iteratively or sequentially operate on sensor data 122 from the sensor 120. The probabilistic updater 220 outputs a probability distribution function (PDF) to a parameter updater or a probabilistic sampler 230, which generates one or more parameters, such as an estimated diagnostic parameter, which is sent to the controller 110, is used as part of an iterative loop as input to the dynamic state-space model 210, and/or is a basis of the output 150. The dynamic state-space model 210 and probabilistic updater 220 are further described, infra.

Figure 3:
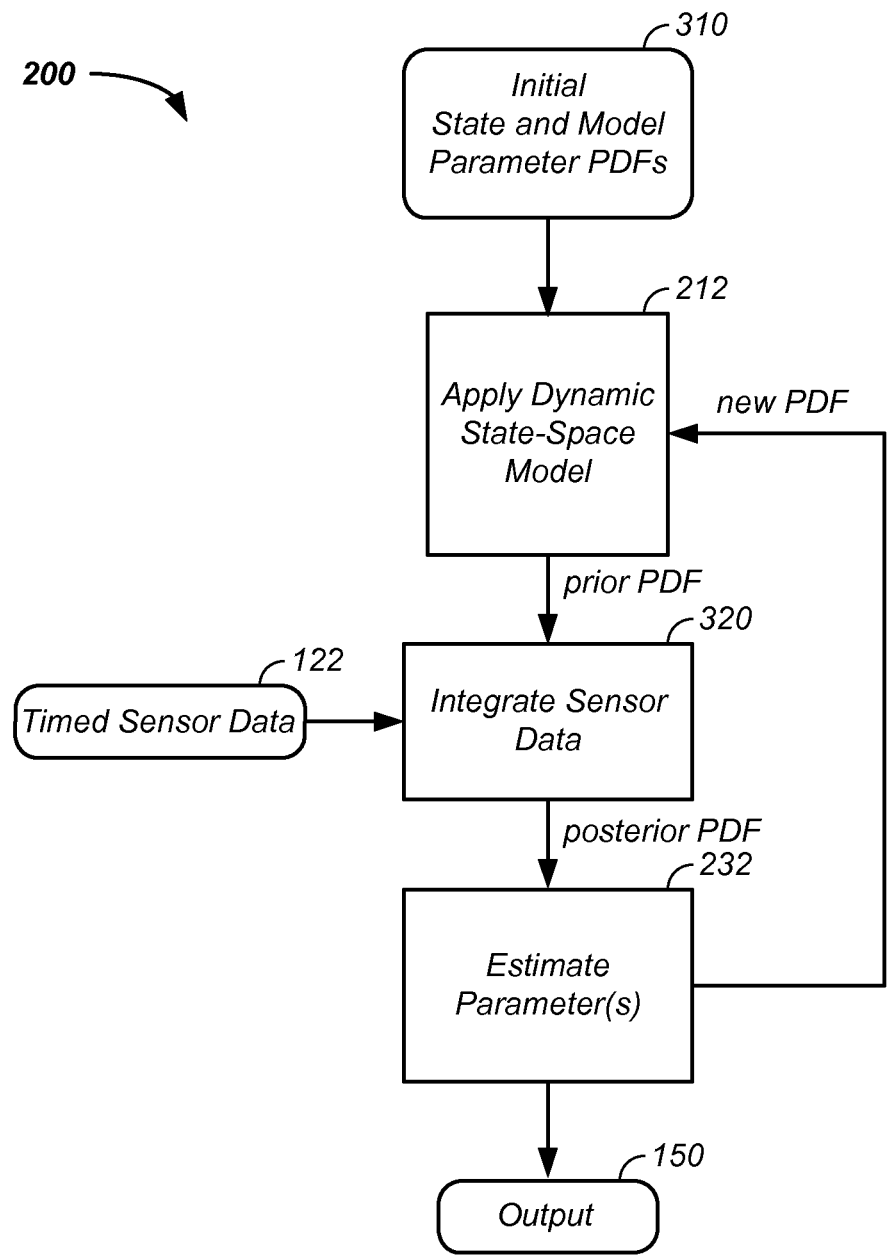
FIG. 3 is a flow diagram of a probabilistic digital signal processor.

Referring now to FIG. 3, the probabilistic digital signal processor 200 is further described. Generally, initial probability distribution functions 310 are input to the dynamic state-space model 210. In a process 212, the dynamic state-space model 210 operates on the initial probability distribution functions 310 to generate a prior probability distribution function, hereinafter also referred to as a prior or as a prior PDF. For example, an initial state parameter 312 probability distribution function and an initial model parameter 314 probability distribution function are provided as initial inputs to the dynamic state-space model 210. The dynamic state-space model 210 operates on the initial state parameter 312 and/or initial model parameter 314 to generate the prior probability distribution function, which is input to the probabilistic updater 220. In a process 320, the probabilistic updater 220 integrates sensor data, such as timed sensor data 122, by operating on it and on the prior probabilistic distribution function to generate a posterior probability distribution function, herein also referred to as a posterior or as a posterior PDF. In a process 232, the probabilistic sampler 230 estimates one or more parameters using the posterior probability distribution function. The probabilistic sampler 230 operates on the state and model parameter probability distribution functions from the state and model parameter updaters 224, 226, respectively or alternatively operates on the joint parameter probability distribution function and calculates an output. The output is optionally:

the state or joint parameter PDF, passed to the PDF resampler 520; and/or output values resulting from an operation on the inputs to the output 150 or output display or the 110 controller In one example, expectation values such as mean and standard deviation of a state parameter are calculated from the state parameter PDF and output to the user, such as for diagnosis. In another example, expectation values, such as the mean value of state and model parameters, are calculated and then used in a model to output a more advanced diagnostic or prognostic parameter. In a third example, expectation values are calculated on a PDF that is the result of an operation on the state parameter PDF and/or model parameter PDF. Optionally, the output is the same as the state parameter PDF or model parameter PDF. Other data, such as user-input data, is optionally used in the output operation. The estimated parameters of the probabilistic sampler 230 are optionally used as a feedback to the dynamic state-space model 210 or are used to estimate a biomedical parameter. The feedback to the dynamic state-space model 210 is also referred to as a new probability function or as a new PDF, which is/are updates of the initial state parameter 312 and/or are updates of the initial model parameter 314. Again, for clarity, an example of an estimated parameter 232 is a measurement of the heart/cardiovascular system, such as heartbeat stroke volume.

Dual Estimator

Figure 4:
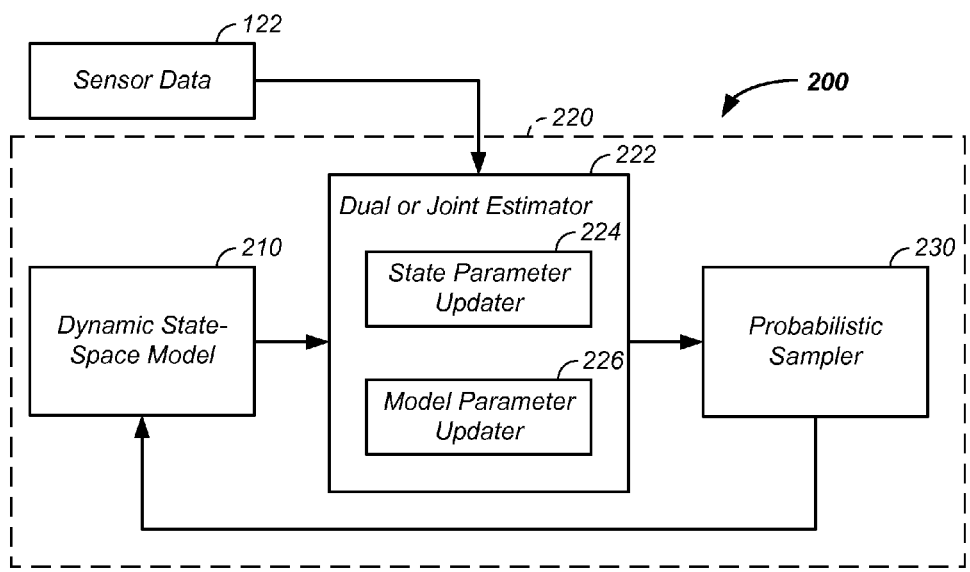
FIG. 4 illustrates a dual estimator.

In another embodiment, the probabilistic updater 220 of the probabilistic digital signal processor 200 uses a dual or joint estimator 222. Referring now to FIG. 4, the joint estimator 222 or dual estimation process uses both a state parameter updater 224 and a model parameter updater 226. Herein, for clarity, a dual estimator 222 is described. However, the techniques and steps described herein for the dual estimator are additionally applicable to a joint estimator as the state parameter and model parameter vector and/or matrix of the dual estimator are merely concatenated in a joint parameter vector and/or are joined in a matrix in a joint estimator.

State Parameter Updater

A first computational model used in the probabilistic updater 220 includes one or more state variables or state parameters, which correspond to the parameter being estimated by the state parameter updater 224. In the case of the hemodynamics monitoring apparatus, state parameters include time, intensity, reflectance, and/or a pressure. Some or all state parameters are optionally chosen such that they represent the 'true' value of noisy timed sensor data. In this case, calculation of such a posterior state parameter PDF constitutes a noise filtering process and expectation values of the PDF optionally represent filtered sensor values and associated confidence intervals.

Model Parameter Updater

A second computational model used in the probabilistic updater 220 includes one or more model parameters updated in the model parameter updater 226. For example, in the case of the hemodynamics monitoring apparatus, model parameters include time interval, a heart rate, a stroke volume, and/or a blood oxygenation percentage.

Hence, the dual estimator 222 optionally simultaneously or in an iterative loop updates or calculates one or both of the state parameters and model parameters. The probabilistic sampler 230 is used to determine the estimated value for the biomedical parameter, which is optionally calculated from a state parameter, a model parameter, or a combination of one or more of the state parameter and/or model parameter.

Figure 5:
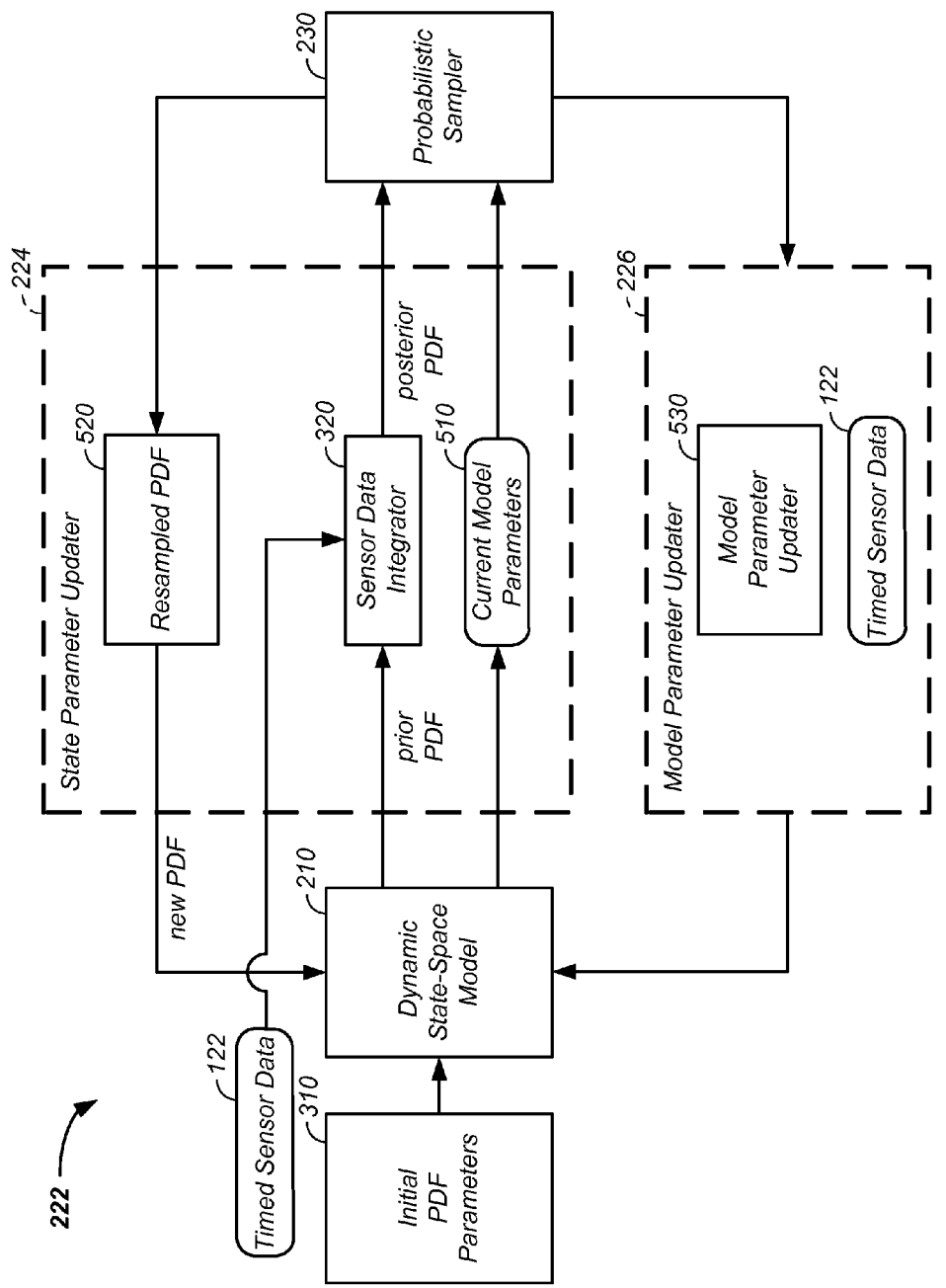
FIG. 5 expands the dual estimator.

Referring still to FIGS. 3 and 4 and now referring to FIG. 5, a first example of the dual estimator 222 is described and placed into context of the dynamic state-space model 210 and probabilistic sampler 230 of the probabilistic digital signal processor 200. The state parameter updater 224 element of the dual estimator 222 optionally:

uses a sensor data integrator 320 operating on the prior PDF being passed from the dynamic state-space model 210, and optionally operates on new timed sensor data 122, to produce the posterior PDF passed to the probabilistic sampler 230;

operates on current model parameters 510; and/or in a process 520, the state parameter updater 224 optionally re-samples a probability distribution function passed from the probabilistic sampler 230 to form the new probability distribution function passed to the dynamic state-space model 210.

In addition, in a process 530 the model parameter updater 226 optionally integrates new timed sensor data 122 with output from the probabilistic sampler 230 to form new input to the dynamic state-space model 210.

Figure 6:
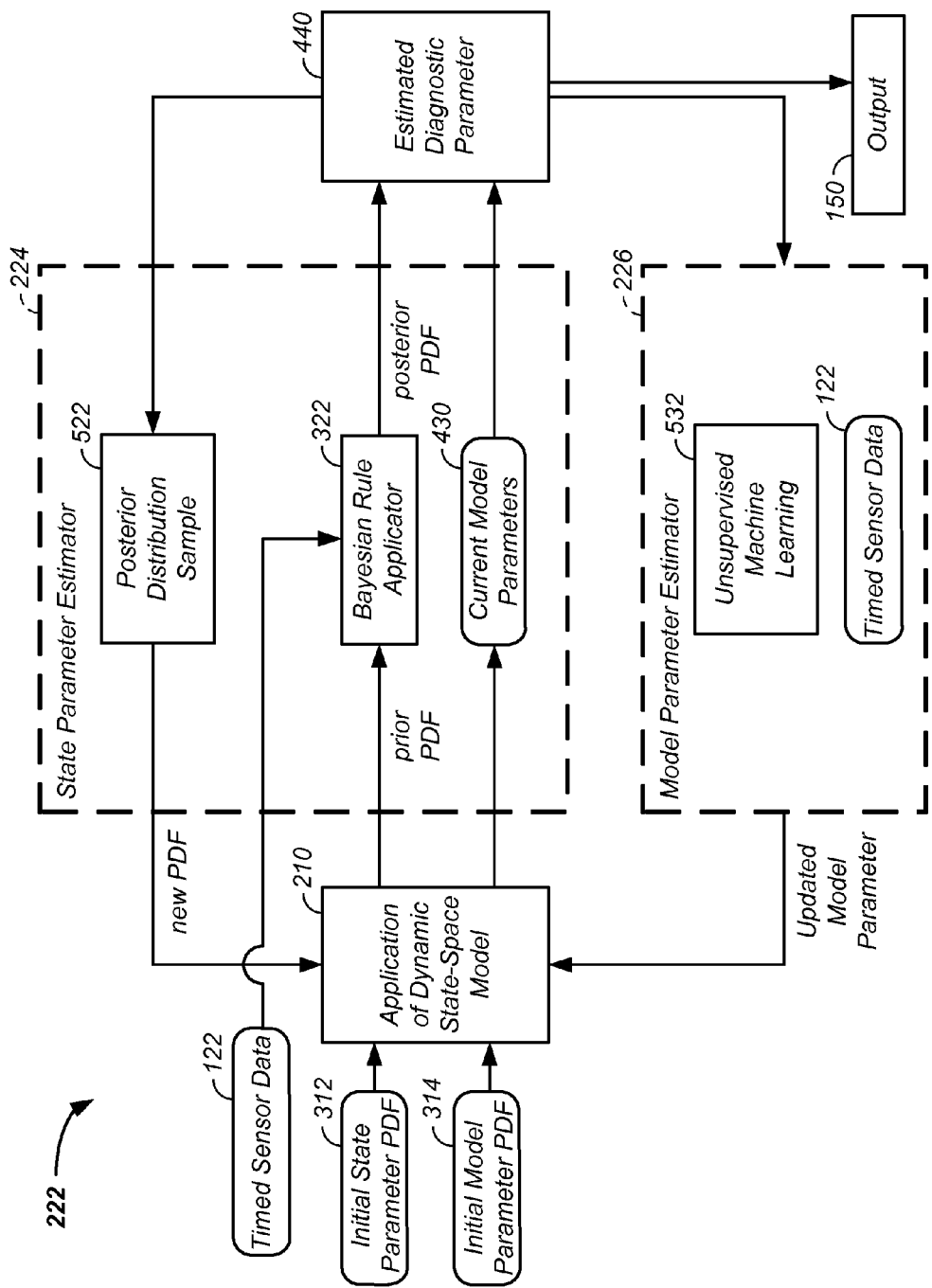
FIG. 6 illustrates state and model parameter estimators.

Referring now to FIG. 6, a second example of a dual estimator 222 is described. In this example:
initial state parameter probability distribution functions 312 are passed to the dynamic state-space model 210; and/or
initial model parameter probability distribution functions 314 are passed to the dynamic state-space model 210;
Further, in this example:
a Bayesian rule applicator 322 is used as an algorithm in the sensor data integrator 320;
a posterior distribution sample algorithm 522 is used as the algorithm in the resampling of the PDF process 520; and
a supervised or unsupervised machine learning algorithm 532 is used as the algorithm in the model parameter updater 530.

Filtering

In various embodiments, algorithms, data handling steps, and/or numerical recipes are used in a number of the steps and/or processes herein. The inventor has determined that several algorithms are particularly useful: sigma point Kalman filtering, sequential Monte Carlo, and/or use of a sampler. In a first example, either the sigma point Kalman filtering or sequential Monte Carlo algorithms are used in generating the probability distribution function. In a second example, either the sigma point Kalman filtering or sequential Monte Carlo algorithms are used in the unsupervised machine learning 532 step in the model parameter updater 530 to form an updated model parameter. The sigma point Kalman filtering, sequential Monte Carlo algorithms, and use of a sampler are further described, infra.

Sigma Point Kalman Filter

Filtering techniques based on Kalman and extended Kalman techniques offer advantages over conventional methods and work well for filtering linear systems or systems with small nonlinearities and Gaussian noise. These Kalman filters, however, are not optimum for filtering highly nonlinear systems and/or non-Gaussian/non-stationary noise. In stark contrast, sigma point Kalman filters are well suited to data having nonlinearities and non-Gaussian noise.

Herein, a sigma point Kalman filter (SPKF) refers to a filter using a set of weighted sigma-points that are deterministically calculated, such as by using the mean and square-root decomposition, or an equivalent, of the covariance matrix of a probability distribution function to about capture or completely capture at least the first and second order moments. The sigma-points are subsequently propagated in time through the dynamic state-space model 210 to generate a prior sigma-point set. Then, prior statistics are calculated using tractable functions of the propagated sigma-points and weights, and new measurements.

Sigma point Kalman filter advantages and disadvantages are described herein. A sigma point Kalman filter interprets a noisy measurement in the context of a mathematical model describing the system and measurement dynamics. This gives the sigma point Kalman filter inherent superior performance to all 'model-less' methods, such as Wiener filtering, wavelet de-noising, principal component analysis, independent component analysis, nonlinear projective filtering, clustering methods, adaptive noise cancelling, and many others.

A sigma point Kalman filter is superior to the basic Kalman filter, extended Kalman filter, and related variants of the Kalman filters. The extended Kalman filter propagates the random variable using a single measure, usually the mean, and a first order Taylor expansion of the nonlinear dynamic state-space model 210. Conversely, a sigma point Kalman filter decomposes the random variable into distribution moments and propagates those using the unmodified nonlinear dynamic state-space model 210. As a result, the sigma point Kalman filter yields higher accuracy with equal algorithm complexity, while also being easier to implement in practice.

In the sigma-point formalism the probability distribution function is represented by a set of values called sigma points, those values represent the mean and other moments of the distribution which, when input into a given function, recovers the probability distribution function.

Sequential Monte Carlo

Sequential Monte Carlo (SMC) methods approximate the prior probability distribution function through use of a set of weighted sample values without making assumptions about its form. The samples are then propagated in time through the unmodified dynamic state-space model 210. The resulting samples are used to update the posterior via Bayes rule and the latest noisy measurement or timed sensor data 122.

In the sequential Monte Carlo formalism the PDF is actually discretized into a collection of probability "particles" each representing a segment of the probability density in the probability distribution function.

SPKF and SMC

In general, sequential Monte Carlo methods have analysis advantages compared to the sigma point Kalman filters, but are more computationally expensive. However, the SPKF uses a sigma-point set, which is an exact representation only for Gaussian probability distribution functions (PDFs). As a result, SPKFs lose accuracy when PDFs depart heavily from the Gaussian form, such as with bimodal, heavily-tailed, or nonstationary distributions. Hence, both the SMC and SPKF filters have advantages. However, either a SMC or SPKF is used to propagate the prior using the unmodified DSSM. Herein, generally when a SMC filter is used a SPKF filter is optionally used and vise-versa.

A SPKF or SMC algorithm is used to generate a reference signal in the form of a first probability distribution from the model's current (time=t) physiological state. The reference signal probability distribution and a probability distribution generated from a measured signal from a sensor at a subsequent time (time=t+n) are convoluted using Bayesian statistics to estimate the true value of the measured physiological parameter at time=t+n. The probability distribution function is optionally discrete or continuous. The probability distribution function is optionally used to identify the probability of each value of an unidentified random variable (discrete) or the probability of the value falling within a particular interval (continuous).

In one embodiment, optionally an estimation filter operates on the prior probability distribution function, having an initial distribution, in generation of the posterior probability distribution function, where the posterior probability distribution function has a model parameter distribution that is narrower than the initial distribution.

Characteristic Samplers

Probability distribution functions (PDFs) are optionally continuous or discrete. In the continuous case the probability distribution function is represented by a function. In the discrete case, the variable space is binned into a series of discrete values. In both the continuous and discrete cases, probability distribution functions are generated by first decomposing the PDF into a set of samplers that are characteristic of the probability distribution function and then propagating those samplers via computations through the DSSM (prior generation) and sensor data integrator (posterior generation). Herein, a sampler is a combination of a value and label. The value is associated with the x-axis of the probability distribution function, which denotes state, model, or joint parameters. The label is associated with the y-axis of the probability distribution function, which denotes the probability. Examples of labels are: weight, frequency, or any arbitrary moment of a given distribution, such as a first Gaussian moment. A powerful example of characteristic sampler use is decomposing the PDF into a series of state values with attached first Gaussian moment labels. This sum of several Gaussian distributions with different values and moments usually gives accurate approximations of the true probability distribution function.

Probabilistic Digital Signal Processor

As described, supra, in various embodiments, the probabilistic digital signal processor 200 comprises one or more of a dynamic state-space model 210, a dual or joint estimator 222, and/or a probabilistic sampler 230, which processes input data, such as sensor data 122 and generates an output 150. Preferably, the probabilistic digital signal processor 200 (1) iteratively processes the data and/or (2) uses a physical model in processing the input data.

The probabilistic digital signal processor 200 optionally:
operates using data from a medical meter, where the medical meter yields a first physical parameter from raw data, to generate a second physical parameter not output by the medical meter;
operates on discrete/non-probabilistic input data from a medical device to generate a probabilistic output function;
iteratively circulates a probability distribution function through at least two of the dynamic state-space model, the dual or joint updater, and/or the probabilistic sampler;
fuses or combines output from multiple medical devices; and
prognosticates probability of future events.

A hemodynamics example of a probabilistic digital signal processor 200 operating on data from a pulse oximeter is used to describe these processes, infra.

Dynamic State-Space Model

The dynamic state-space model 210 is further described herein.

Figure 7:
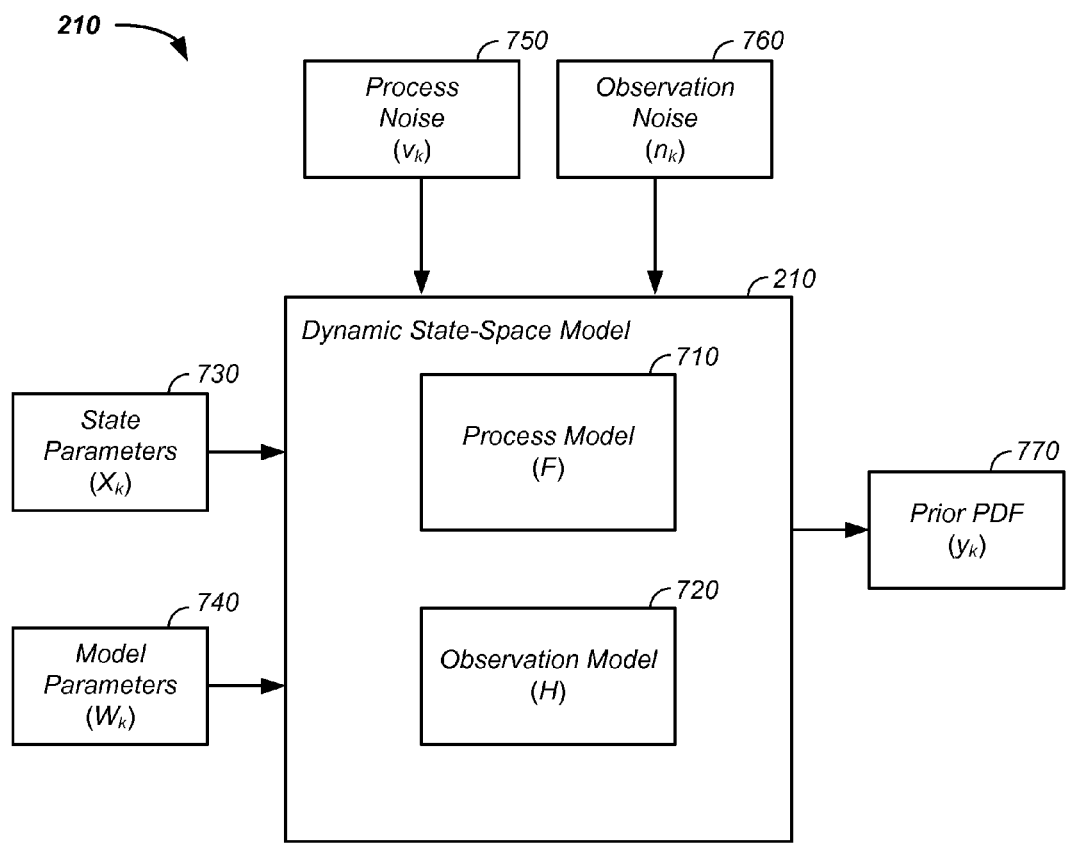
FIG. 7 provides inputs and internal operation of a dynamic state-space model.

Referring now to FIG. 7, schematics of an exemplary dynamic state-space model 210 (DSSM) used in the processing of data is provided. The dynamic state-space model 210 typically and optionally includes a process model 710 and/or an observation model 720. The process model 710, F, which mathematically represents mechanical processes involved in generating one or more biomedical parameters, is measured by a sensor and/or a sensor sensing a mechanical element and describes the state of the biomedical apparatus, output of the biomedical apparatus, and/or state of the patient over time in terms of state parameters. This mathematical model optimally includes mathematical representations accounting for process noise 750, such as mechanically caused artifacts that may cause the sensor to produce a digital output that does not produce an accurate measurement for the biomedical parameter being sensed. The dynamic state-space model 210 also comprises an observational model 720, H, which mathematically represents processes involved in collecting sensor data measured by the mechanical sensor. This mathematical model optimally includes mathematical representations accounting for observation noise produced by the sensor apparatus that may cause the sensor to produce a digital output that does not produce an accurate measurement for a biomedical parameter being sensed. Noise terms in the mathematical models are not required to be additive.

While the process and observational mathematical models 710, 720 are optionally conceptualized as separate models, they are preferably integrated into a single mathematical model that describes processes that produce a biomedical parameter and processes involved in sensing the biomedical parameter. The integrated process and observation model, in turn, is integrated with a processing engine within an executable program stored in a data processor, which is configured to receive digital data from one or more sensors and to output data to a display and/or another output format.

Still referring to FIG. 7, inputs into the dynamic state-space model 210 include one or more of:
state parameters 730, such as the initial state parameter probability distribution function 312 or the new PDF;
model parameters 740, such as the initial noise parameter probability distribution function 314 or an updated model parameter from the unsupervised machine learning module 532;
process noise 750; and/or
observation noise 760.

Hemodynamics Dynamic State-Space Model

Figure 8:
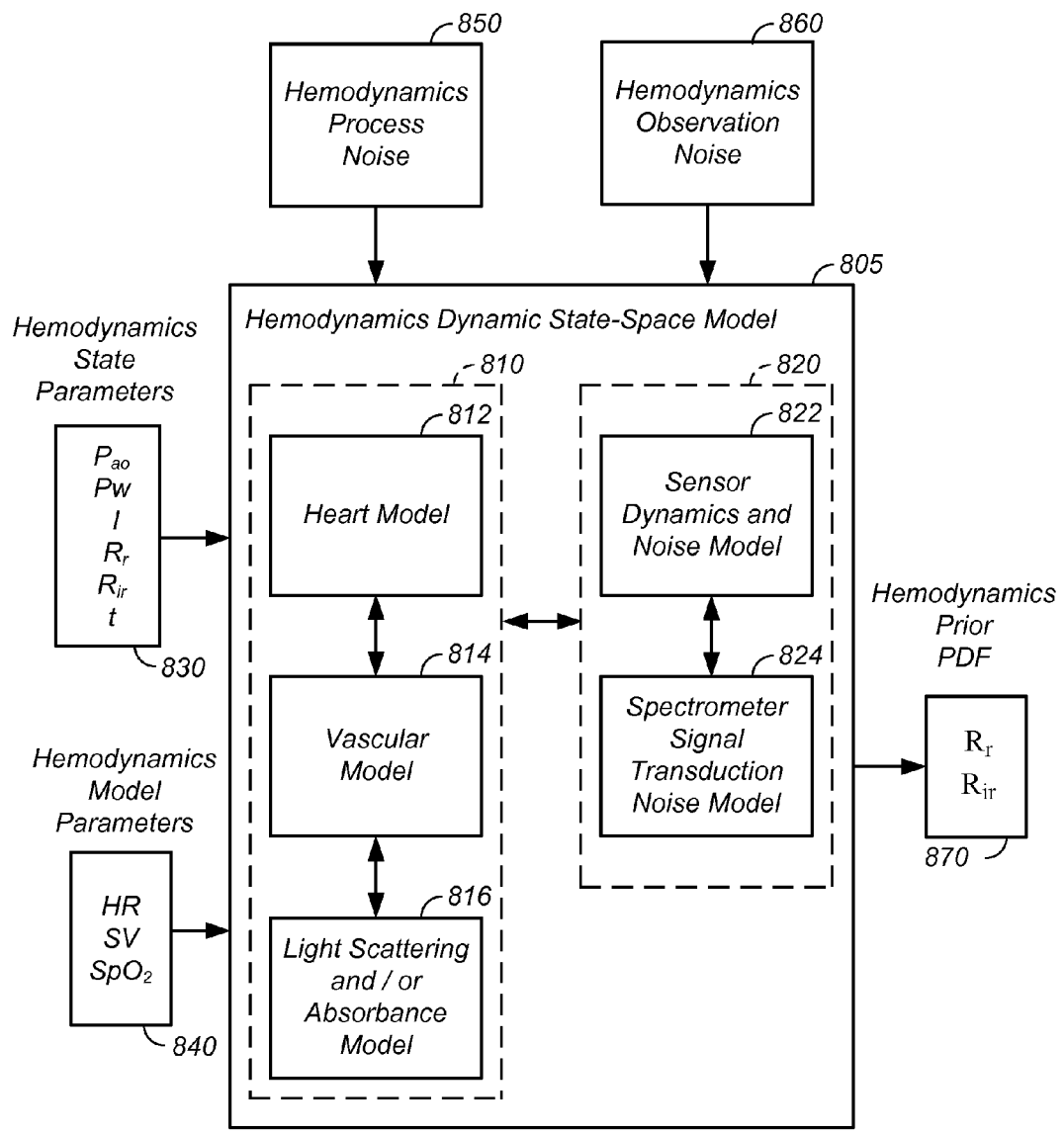
FIG. 8 is a flow chart showing the components of a hemodynamics dynamic state-space model.
Figure 9A:
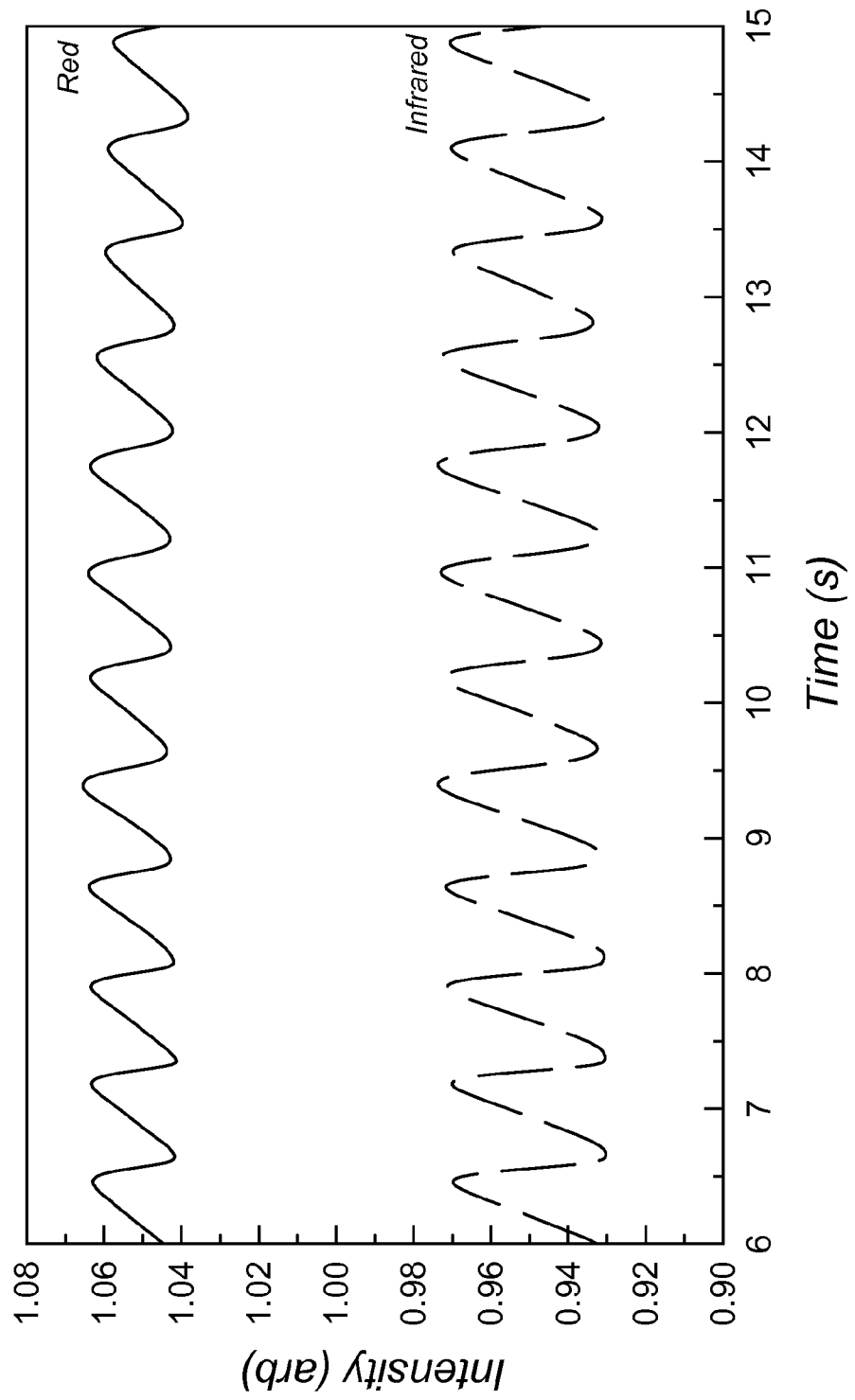
FIG. 9 is a chart showing input sensor data, FIG. 9A; processed output data of heart rate, FIG. 9B; stroke volume, FIG. 9C; cardiac output, FIG. 9D; oxygen, FIG. 9E; and pressure, FIG. 9F from a data processor configured to process pulse oximetry data.
Figure 9D:
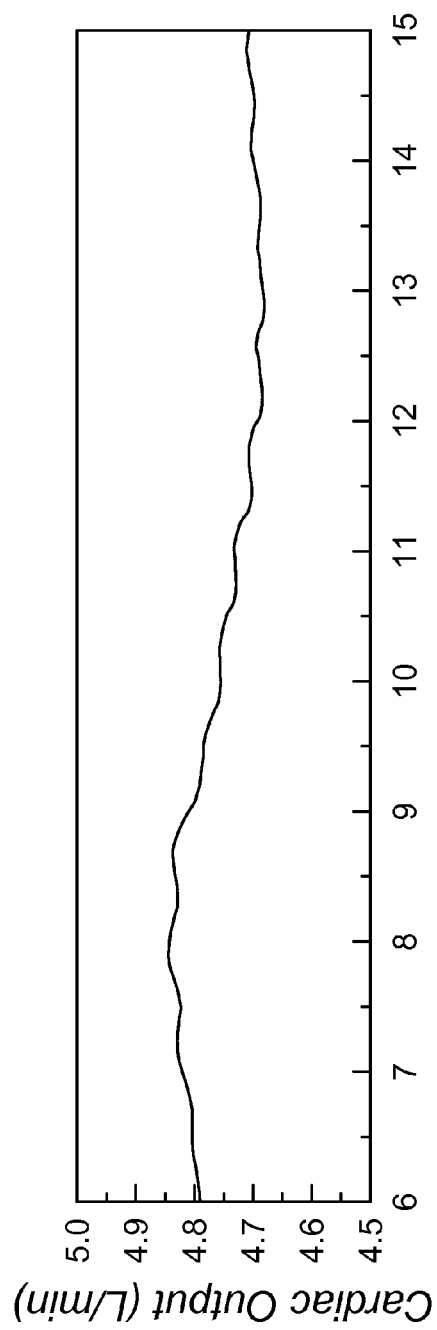
Figure 9E:
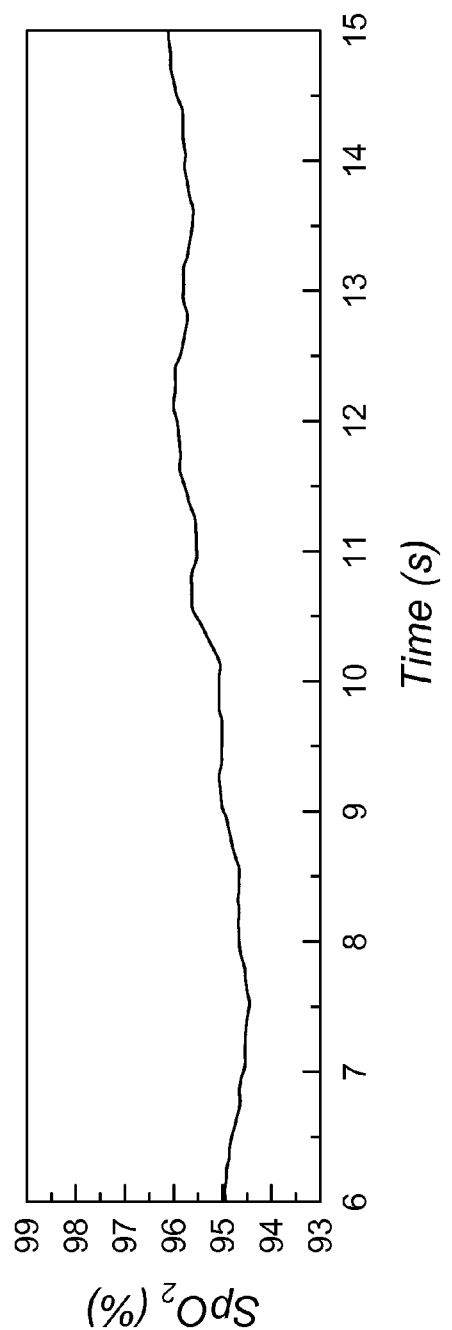
Figure 9F:
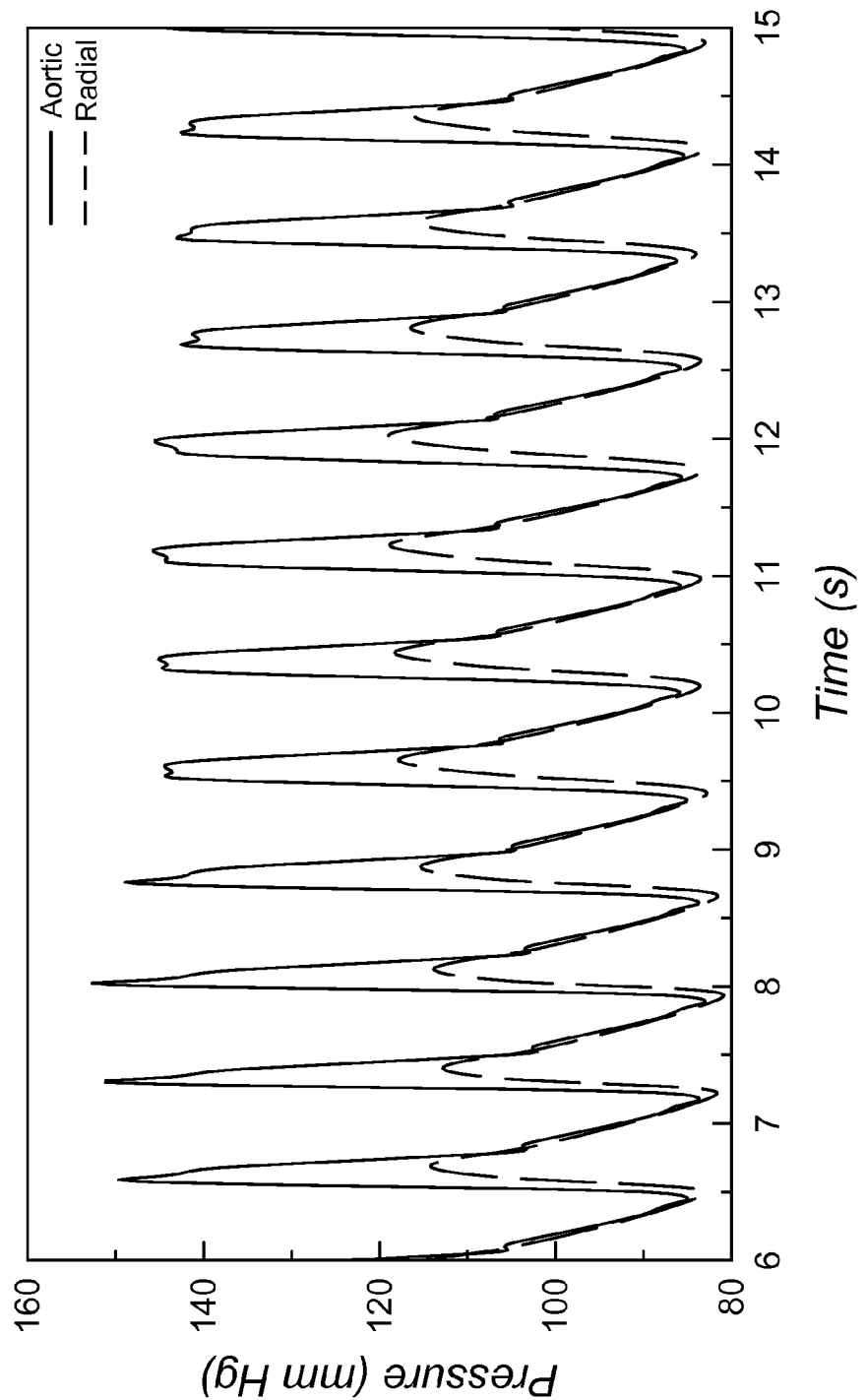
Figure 10A:
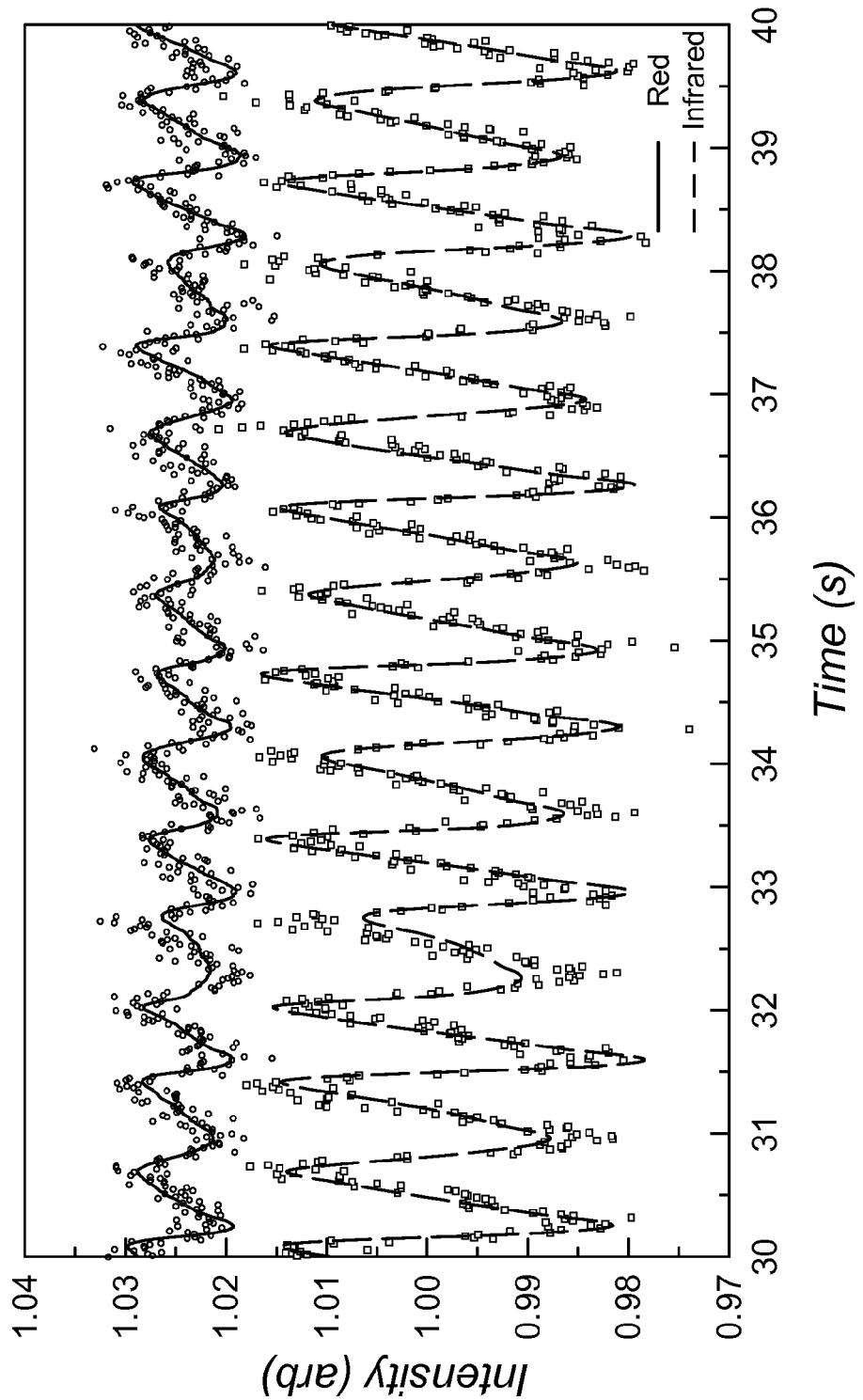
FIG. 10 is a chart showing input sensor data, FIG. 10A, and processed output data, FIGS. 10A-10E, from a data processor configured to process pulse oximetry data under a low blood perfusion condition.
Figure 10B:
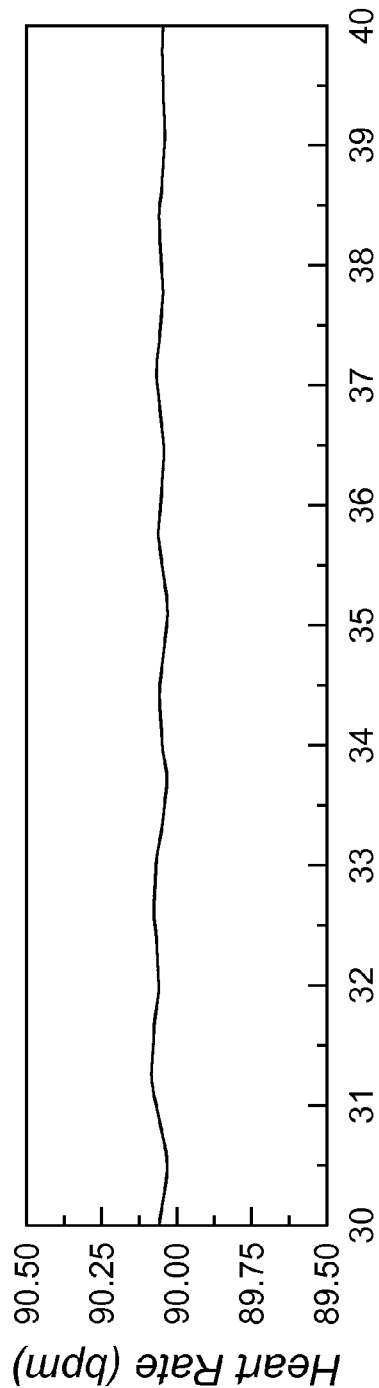
Figure 10C:
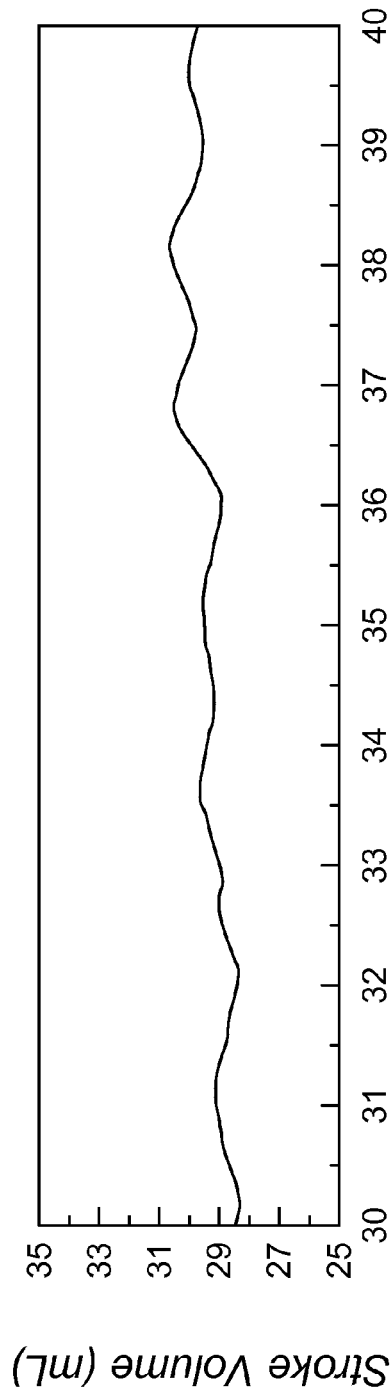
Figure 10D:
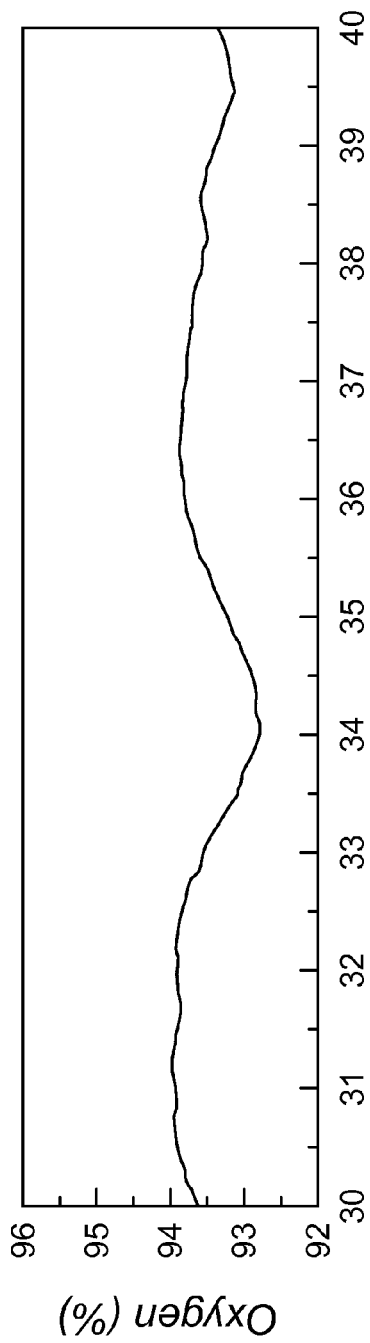
Figure 10E:
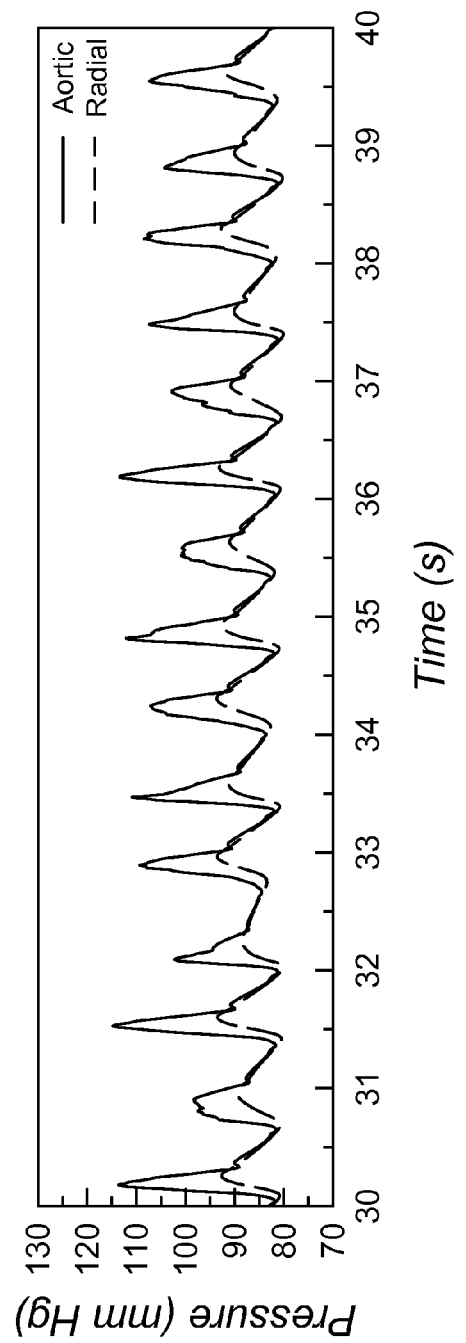

A first non-limiting specific example is used to facilitate understanding of the dynamic state-space model 210. Referring now to FIG. 8, a hemodynamics dynamic state-space model 805 flow diagram is presented. Generally, the hemodynamics dynamic state-space model 805 is an example of a dynamic state-space model 210. The hemodynamics dynamic state-space model 805 combines sensor data 122, such as a spectral readings of skin, with a physical parameter based probabilistic model. The hemodynamics dynamic state-space model 805 operates in conjunction with the probabilistic updater 220 to form an estimate of heart/cardiovascular state parameters.

To facilitate description of the probabilistic digital signal processor, a non-limiting example of a hemodynamics process model is provided. In this example, the probabilistic digital signal processor is provided:
raw sensor data, such as current, voltage, and/or resistance; and/or
a first physical parameter output from a medical device.

In this example, the medical device is a pulse oximeter collecting raw data and the first physical parameter from the pulse oximeter provided as input to the probabilistic digital signal processor is one or more of:
a heart rate; and/or
a blood oxygen saturation.

The probabilistic digital signal processor uses a physical model, such as a probabilistic model, to operate on the first physical parameter and/or the raw data to generate a second physical parameter, where the second physical parameter is not the first physical parameter. For example, the output of the probabilistic digital signal processor using a physical hemodynamic models, when provided with the pulse oximeter data, is one or more of:
a heart stroke volume;
a cardiac output flow rate;
an aortic blood pressure; and/or
a radial blood pressure.

Optionally, the output from the probabilistic model is an updated, error filtered, and/or smoothed version of the original input data, such as a smoothed blood oxygen saturation percentage as a function of time.

Still referring to FIG. 8, to facilitate description of the hemodynamics dynamic state-space model 805, a non-limiting example is provided. In this example, the hemodynamics dynamic state-space model 805 is further described. The hemodynamics dynamic state-space model 805 preferably includes a hemodynamics process model 810 corresponding to the dynamic state space model 210 process model 710. Further, the hemodynamics dynamic state-space model 805 preferably includes a hemodynamics observation model 820 corresponding to the dynamic state space model 210 observation model 720. The hemodynamics process model 810 and hemodynamics observation model 820 are further described, infra.

Still referring to FIG. 8, the hemodynamics process model 810 optionally includes one or more of a heart model 812, a vascular model 814, and/or a light scattering or a light absorbance model 816. The heart model 812 is a physics based probabilistic model of the heart and movement of blood in and/or from the heart. The vascular model 814 is a physics based probabilistic model of movement of blood in arteries, veins, and/or capillaries. The various models optionally share information. For example, blood flow or stroke volume exiting the heart in the heart model 812 is optionally an input to the arterial blood in the vascular model 814. The light scattering and/or absorbance model 816 relates spectral information, such as from a pulse oximeter, to additional hemodynamics dynamic state-space model parameters, such as heart rate (HR), stroke volume (SV), and/or whole-blood oxygen saturation ($SpO_2$) or oxyhemoglobin percentage.

Still referring to FIG. 8, the hemodynamics observation model 820 optionally includes one or more of a sensor dynamics and noise model 822 and/or a spectrometer signal transduction noise model 824. Each of the sensor dynamics and noise model 822 and the spectrometer signal transduction noise model 824 are physics based probabilistic models related to noises associated with the instrumentation used to collect data, environmental influences on the collected data, and/or noise due to the human interaction with the instrumentation, such as movement of the sensor. As with the hemodynamics process model 810, the sub-models of the hemodynamics observation model 820 optionally share information. For instance, movement of the sensor noise is added to environmental noise. Optionally and preferably, the hemodynamics observation model 820 shares information with and/provides information to the hemodynamics process model 810.

The hemodynamics dynamic state-space model 805 receives inputs, such as one or more of:
hemodynamics state parameters 830;
hemodynamics model parameters 840;
hemodynamics process noise 850; and
hemodynamics observation noise 860.

Examples of hemodynamics state parameters 830, corresponding to state parameters 730, include: radial pressure ($P_w$), aortic pressure ($P_{ao}$), time (t), a spectral intensity (I) or a related absorbance value, a reflectance or reflectance ratio, such as a red reflectance ($R_r$) or an infrared reflectance ($R_{ir}$), and/or a spectral intensity ratio ($I_R$). Examples of hemodynamics model parameters 840, corresponding to the more generic model parameters 740, include: heart rate (HR), stroke volume (SV), and/or whole-blood oxygen saturation ($SpO_2$). In this example, the output of the hemodynamics dynamic state-space model 805 is a prior probability distribution function with parameters of one or more of the input hemodynamics state parameters 830 after operation on by the heart dynamics model 812, a static number, and/or a parameter not directly measured or output by the sensor data. For instance, an input data stream is optionally a pulse oximeter yielding spectral intensities, ratios of intensities, and a percent oxygen saturation. However, the output of the hemodynamics dynamic state-space model is optionally a second physiological value, such as a stroke volume of the heart, which is not measured by the input biomedical device.

The hemodynamics dynamic state-space model 805 optionally receives inputs from one or more additional models, such as an irregular sampling model, which relates information collected at irregular or non-periodic intervals to the hemodynamics dynamic state-space model 805.

Generally, the hemodynamics dynamic state-space model 805 is an example of a dynamic state-space model 210, which operates in conjunction with the probabilistic updater 220 to form an estimate of a heart state parameter and/or a cardiovascular state parameter.

Generally, the output of the probabilistic signal processor 200 optionally includes a measure of uncertainty, such as a confidence interval, a standard deviation and/or a standard error. Optionally, the output of the probabilistic signal processor 200 includes:
a filtered or smoothed version of the parameter measured by the medical meter; and/or
a probability function associated with a parameter not directly measured by the medical meter.

Example I

An example of a pulse oximeter with probabilistic data processing is provided as an example of the hemodynamics dynamic state-space model 805. The model is suitable for processing data from a pulse oximeter model. In this example, particular equations are used to further describe the hemodynamics dynamic state-space model 805, but the equations are illustrative and non-limiting in nature.

Heart Model

An example of the heart model 812 is used to further described an example of the hemodynamics dynamic state-space model 805. In this example, cardiac output is represented by equation 1, $$Q_{CO}(t) = \overline{Q}_{CO} \sum_{1}^{\delta} a_k \exp\left[\frac{-(t-b_k)^2}{c_k^2}\right] \quad (1)$$

where cardiac output $Q_{co}(t)$, is expressed as a function of heart rate (HR) and stroke volume (SV) and where $Q_{co}$=(HR× SV)/60. The values $a_k$, $b_k$, and $c_k$ are adjusted to fit data on human cardiac output.

Vascular Model

An example of the vascular model 814 of the hemodynamics state-space model 805 is provided. The cardiac output function pumps blood into a Windkessel 3-element model of the vascular system including two state variables: aortic pressure, $P_{ao}$, and radial (Windkessel) pressure, $P_w$, according to equations 2 and 3, $$P_{w,k+1} = \frac{1}{C_w R_p}((R_P + Z_0)Q_{CO} - P_{CO,k})\delta t + P_{w,k} \quad (2)$$

$$P_{ao,k+1} = P_{w,k+1} + Z_0 Q_{CO} \quad (3)$$

where $R_p$ and $Z_o$ are the peripheral resistance and characteristic aortic impedance, respectively. The sum of these two terms is the total peripheral resistance due to viscous (Poiseuille-like) dissipation according to equation 4, $$Z_0 = \sqrt{\rho/AC_l} \quad (4)$$

where ρ is blood density and $C_l$ is the compliance per unit length of artery. The elastic component due to vessel compliance is a nonlinear function including thoracic aortic cross-sectional area, A: according to equation 5, $$A(P_{CO}) = A_{max}\left[\frac{1}{2} + \frac{1}{\pi}\arctan\left(\frac{P_{CO} - P_0}{P_1}\right)\right] \quad (5)$$

where $A_{max}$, $P_0$, and $P_1$ are fitting constants correlated with age and gender according to equations 6-8.

$$A_{max} = (5.62 - 1.5(\text{gender})) \cdot \text{cm}^2 \quad (6)$$

$$P_0 = (76 - 4(\text{gender}) - 0.89(\text{age})) \cdot \text{mmHg} \quad (7)$$

$$P_1 (57 - 0.44(\text{age})) \cdot \text{mmHg} \quad (8)$$

The time-varying Windkessel compliance, $C_w$, and the aortic compliance per unit length, $C_l$, are related in equation 9, $$C_w = lC_1 = l\frac{dA}{dP_\infty} = l\frac{A_{max}/(\pi P_1)}{1 + \left(\frac{P_\infty - P_0}{P_1}\right)} \quad (9)$$

where l is the aortic effective length. The peripheral resistance is defined as the ratio of average pressure to average flow. A set-point pressure, $P_{set}$, and the instantaneous flow are related to the peripheral resistance, $R_p$, according to equation 10, $$R_P = \frac{P_{set}}{(HR \cdot SV)/60} \quad (10)$$

are used to provide compensation to autonomic nervous system responses. The value for $P_{set}$ is optionally adjusted manually to obtain 120 over 75 mmHg for a healthy individual at rest.

Light Scattering and Absorbance Model

The light scattering and absorbance model 816 of the hemodynamics dynamic state-space model 805 is further described. The compliance of blood vessels changes the interactions between light and tissues with pulse. This is accounted for using a homogenous photon diffusion theory for a reflectance or transmittance pulse oximeter configuration according to equation 11, $$R = \frac{I_{ac}}{I_{dc}} = \frac{\Delta I}{I} = \frac{3}{2}\sum_s^1 K(\alpha, d, r) \sum_a^{art} \Delta V_0 \quad (11)$$

for each wavelength. In this example, the red and infrared bands are centered at about 660±100 nm and at about 880±100 nm. In equation 11, 1 (no subscript) denotes the detected intensity, R, is the reflected light, and the, $I_{ac}$, is the pulsating or ac intensity or signal, $I_{dc}$, is the background or dc intensity, α, is the attenuation coefficient, d, is the illumination length scale or depth of photon penetration into the skin, and, r, is the distance between the source and detector.

Referring again to the vascular model 814, $V_a$ is the arterial blood volume, which changes as the cross-sectional area of illuminated blood vessels, $\Delta A_w$, according to equation 12, $$\Delta V_a \approx r \cdot \Delta A_w \quad (12)$$

where r is the source-detector distance.

Referring again to the light scattering and absorbance model 816, the tissue scattering coefficient, $\Sigma'_s$, is assumed constant but the arterial absorption coefficient, $\Sigma_a^{art}$, which represents the extinction coefficients, depends on blood oxygen saturation, $SpO_2$, according to equation 13, $$\sum_a^{art} = \frac{H}{v_i}[SpO_2 \cdot \sigma_0^{100\%} + (1 - SpO_2) \cdot \sigma_0^{0\%}] \quad (13)$$

which is the Beer-Lambert absorption coefficient, with hematocrit, H, and red blood cell volume, $v_i$. The optical absorption cross-sections, proportional to the absorption coefficients, for red blood cells containing totally oxygenated ($HbO_2$) and totally deoxygenated (Hb) hemoglobin are $\sigma_a^{100\%}$ and $\sigma_a^{0\%}$, respectively.

The function K(α, d, r), along with the scattering coefficient, the wavelength, sensor geometry, and oxygen saturation dependencies, alters the effective optical pathlengths, according to equation 14.

$$K(\alpha, d, r) \approx \frac{-r^2}{1 + \alpha r} \quad (14)$$

The attenuation coefficient α is provided by equation 15, $$\alpha = \sqrt{3\Sigma_a(\Sigma_s + \Sigma_a)} \quad (15)$$

where $\Sigma_a$ and $\Sigma_s$ are whole-tissue absorption and scattering coefficients, respectively, which are calculated from Mie Theory.

Red, $\overline{K_r}$, and infrared, $\overline{K_{ir}}$, K values as a function of $SpO_2$ are optionally represented by two linear fits, provided in equations 16 and 17

$$\overline{K_r} \approx -4.03 \cdot SpO_2 - 1.17 \quad (16)$$

$$\overline{K_{ir}} \approx 0.102 \cdot SpO_2 - 0.753 \quad (17)$$

in $mm^2$. The overbar denotes the linear fit of the original function. Referring yet again to the vascular model 814, the pulsatile behavior of $\Delta A_w$, which couples optical detection with the cardiovascular system model, is provided by equation 18, $$\Delta A_w = \frac{A_{w,max}}{\pi} \frac{P_{w,1}}{P_{w,1}^2 + (P_{w,k+1} - P_{w,0})^2}\Delta P_w \quad (18)$$

with $P_{w,0} = (\frac{1}{3})P_0$ and $P_{w,1} = (\frac{1}{3})P_1$ to account for the poorer compliance of arterioles and capillaries relative to the thoracic aorta. The subscript k is a data index and the subscript k+1 or k+n refers to the next or future data point.

Referring yet again to the light scattering and absorbance models, third and fourth state variables, the red and infrared reflected intensity ratios, $R = I_{ac}/I_{dc}$, are provided by equations 19 and 20.

$$R_{r,k+1} = c\Sigma'_{s,r}\overline{K_r}\Sigma_{a,r}^{art}\Delta A_w + R_{r,k} + v_r \quad (19)$$

$$R_{ir,k+1} = c\Sigma'_{s,ir}\overline{K_{ir}}\Sigma_{a,ir}^{art}\Delta A_w + R_{ir,k} + v_{ir} \quad (20)$$

Here, v is a process noise, such as an added random number or are Gaussian-distributed process noises intended to capture the baseline wander of the two channels, $\Sigma'_{s,r}$ and $\Sigma'_{s,ir}$ are scattering coefficients, and $\Sigma_{a,r}^{art}$ and $\Sigma_{a,ir}^{art}$ are absorption coefficients.

Sensor Dynamics and Noise Model

The sensor dynamics and noise model 822 is further described. The constant c subsumes all factors common to both wavelengths and is treated as a calibration constant. The observation model adds noises, n, with any probability distribution function to $R_r$ and $R_{ir}$, according to equation 21.

$$\begin{bmatrix} y_{r,k} \\ y_{ir,k} \end{bmatrix} = \begin{bmatrix} R_{r,k} \\ R_{ir,k} \end{bmatrix} + \begin{bmatrix} n_{r,k} \\ n_{ir,k} \end{bmatrix} \quad (21)$$

A calibration constant, c, was used to match the variance of the real $I_{ac}/I_{dc}$ signal with the variance of the dynamic state-space model generated signal for each wavelength. After calibration, the age and gender of the patient was entered. Estimates for the means and covariances of both state and parameter PDFs are optionally entered.

Referring now to FIG. 9, processed data from a relatively high signal-to-noise ratio pulse oximeter data source is provided for a fifteen second stretch of data. Referring now to FIG. 9A, input photoplethysmographic waveforms are provided. Using the hemodynamics dynamic state-space model 805, the input waveforms were used to extract heart rate (FIG. 9B), left-ventricular stroke volume (FIG. 9C), cardiac output (FIG. 9D), blood oxygen saturation (FIG. 9E), and aortic and systemic (radial) pressure waveforms (FIG. 9F). Several notable points are provided. First, the pulse oximeter provided a first physical value of a hemoglobin oxygen saturation percentage. However, the output blood oxygen saturation percentage, FIG. 9E, was processed by the probabilistic digital signal processor 200. Due to the use of the sensor dynamics and noise model 822 and the spectrometer signal transduction noise model, noisy data, such as due to ambulatory movement of the patient, is removed in the smoothed and filtered output blood oxygen saturation percentage. Second, some pulse oximeters provide a heart rate. However, in this case the heart rate output was calculated using the physical probabilistic digital signal processor 200 in the absence of a heart rate input data source 122. Third, each of the stroke volume, FIG. 9C, cardiac output flow rate, FIG. 9D, aortic blood pressure, FIG. 9E, and radial blood pressure, FIG. 9E, are second physical parameters that are different from the first physical parameter measured by the pulse oximeter photoplethysmographic waveforms.

Referring now to FIG. 10, a second stretch of photoplethysmographic waveforms are provided that represent a low signal-to-noise ratio signal from a pulse oximeter. Low signal-to-noise photoplethysmographic waveforms (FIG. 10A) were used to extract heart rate (FIG. 10B), left-ventricular stroke volume (FIG. 10C), blood oxygen saturation (FIG. 10D), and aortic and systemic (radial) pressure waveforms (FIG. 10E) using the hemodynamics dynamic state-space model 805. In each case, the use of the probabilistic digital signal processor 200 configured with the optional sensor dynamics and noise model 822 and spectrometer signal transduction model 824 overcame the noisy input stream to yield smooth and functional output data for medical use.

Example II

A second example of a dynamic state-space model 210 coupled with a dual or joint estimator 222 and/or a probabilistic sampler 230 in a probabilistic updater 220 in a medical or biomedical application is provided.

Electrocardiograph with Probabilistic Data Processing

Figure 11:
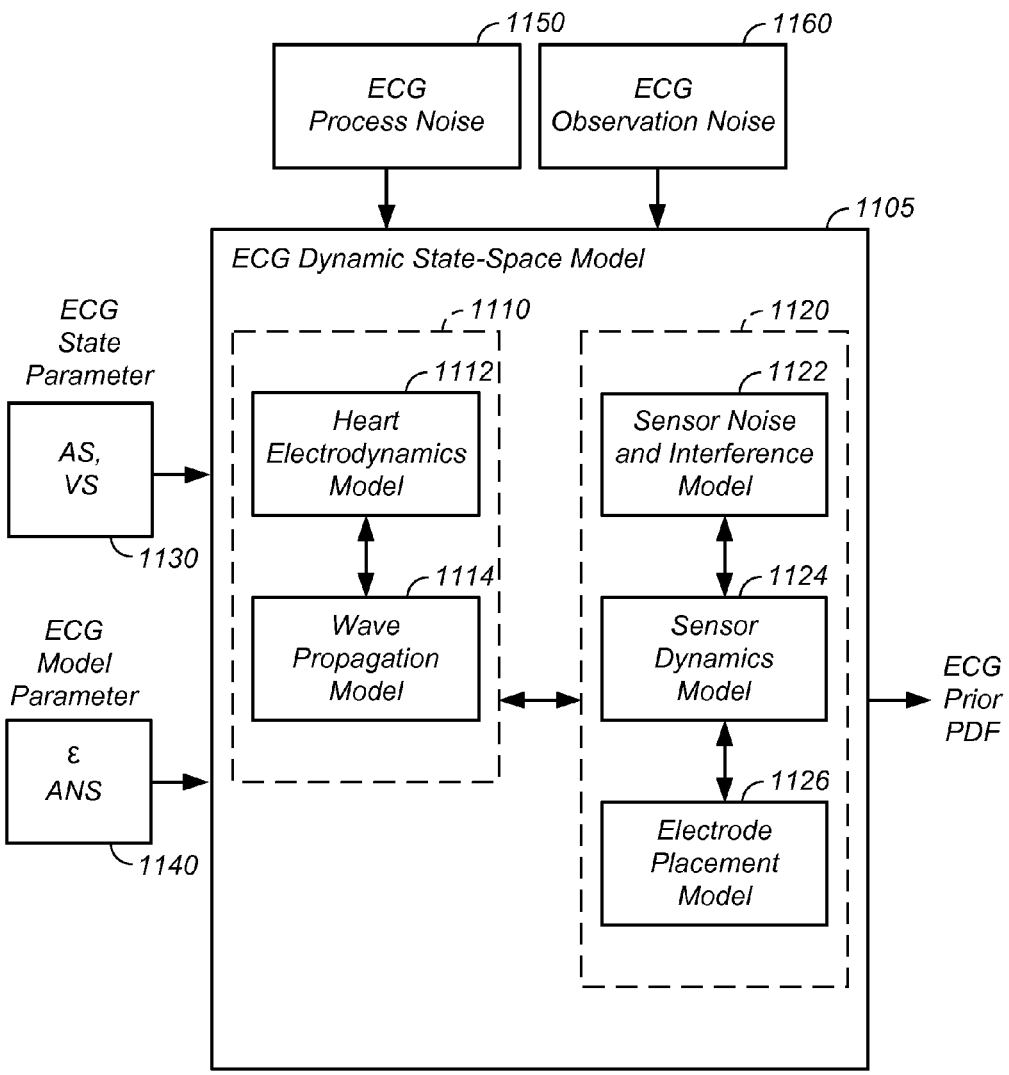
FIG. 11 is a flow chart showing the components of a electrocardiograph dynamic state-space model.

FIG. 11 is a schematic of an electrocardiograph dynamic state-space model suitable for processing electrocardiogram data, including components required to describe the processes occurring in a subject. The combination of SPKF or SMC filtering in state, joint, or dual estimation modes is optionally used to filter electrocardiograph (ECG) data. Any physiology model adequately describing the ECG signal can be used, as well as any model of noise and artifact sources interfering or contaminating the signal. One non-limiting example of such a model is a model using a sum of arbitrary wave functions with amplitude, center and width, respectively, for each wave (P, Q, R, S, T) in an ECG. The observation model includes the state plus additive Gaussian noise, but more realistic pink noise or any other noise distributions can be used.

Still referring to FIG. 11, to facilitate description of the electrocardiograph dynamic state-space model 1105, a non-limiting example is provided. In this example, the electrocardiograph dynamic state-space model 1105 is further described. The electrocardiograph dynamic state-space model 1105 preferably includes a heart electrodynamics model 1110 corresponding to the dynamic state space model 210 process model 710. Further, the electrocardiograph dynamic state-space model 1105 preferably includes a heart electrodynamics observation model 1120 corresponding to the dynamic state space model 210 observation model 720. The electrocardiograph process model 1110 and hemodynamics observation model 1120 are further described, infra.

Still referring to FIG. 11, the electrocardiograph process model 1110 optionally includes one or more of a heart electrodynamics model 1112 and a wave propagation model 1114. The heart electrodynamics model 1112 is a physics based probabilistic model of the electrical output of the heart. The wave propagation model 1114 is a physics based probabilistic model of movement of the electrical pulses through the lungs, fat, muscle, and skin. An example of a wave propagation model 1114 is a thorax wave propagation model modeling electrical wave movement in the chest, such as through an organ. The various models optionally share information. For example, the electrical pulse of the heart electrodynamics model 1112 is optionally an input to the wave propagation model 1114, such as related to one or more multi-lead ECG signals.

Still referring to FIG. 11, the electrocardiogram observation model 1120 optionally includes one or more of a sensor noise and interference model 1122, a sensor dynamics model 1124, and/or an electrode placement model 1126. Each of the sensor noise and interference model 1122 and the sensor dynamics models 1124 are physics based probabilistic models related to noises associated with the instrumentation used to collect data, environmental influences on the collected data, and/or noise due to the human interaction with the instrumentation, such as movement of the sensor. The electrode placement model 1126 relates to placement of the electrocardiograph leads on the body, such as on the arm, leg, or chest. As with the electrocardiograph process model 1110, the sub-models of the electrocardiograph observation model 820 optionally share information. For instance, movement of the sensor noise is added to environmental noise related to changes in room temperature. Optionally and preferably, the electrocardiograph observation model 1120 shares information with and/provides information to the electrocardiograph process model 1110.

The electrocardiograph dynamic state-space model 1105 receives inputs, such as one or more of:
- electrocardiograph state parameters 1130;
- electrocardiograph model parameters 1140;
- electrocardiograph process noise 1150; and
- electrocardiograph observation noise 1160.

Examples of electrocardiograph state parameters 1130, corresponding to state parameters 730, include: atrium signals (AS), ventricle signals (VS) and/or an ECG lead. Examples of electrocardiograph model parameters 1140, corresponding to the more generic model parameters 740, include: permittivity, $\epsilon$, and autonomous nervous system (ANS) tone. In this example, the output of the electrocardiograph dynamic state-space model 1105 is a prior probability distribution function with parameters of one or more of the input electrocardiograph state parameters 1130 after operation on by the heart electrodynamics model 1112, a static number, and/or a parameter not measured or output by the sensor data.

Figure 12A:
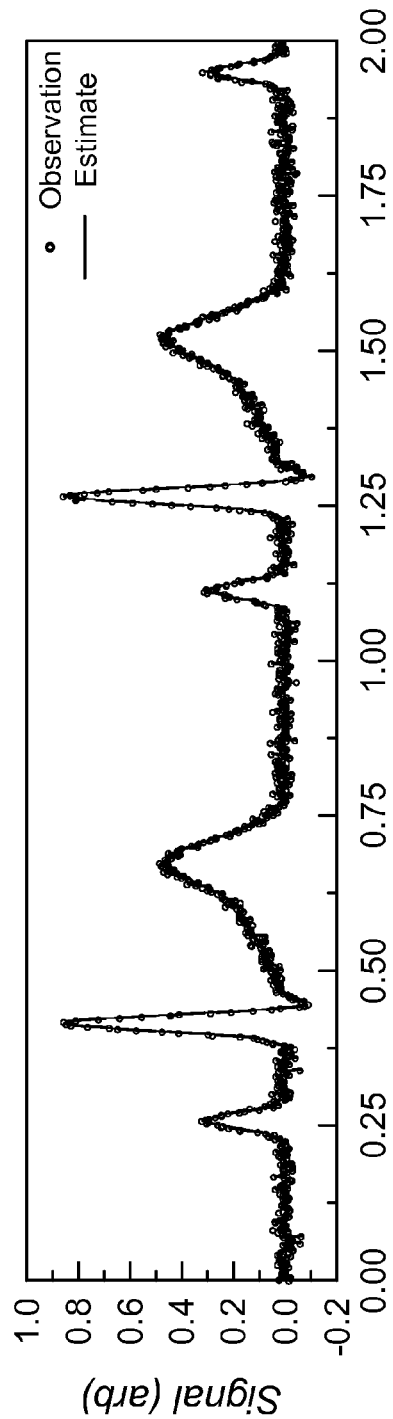
FIG. 12 is a chart showing noisy non-stationary ECG sensor data input, FIG. 12A and FIG. 12B and processed heart rate and ECG output, FIG. 12A and FIG. 12B, for a data processor configured to process ECG sensor data.
Figure 12B:
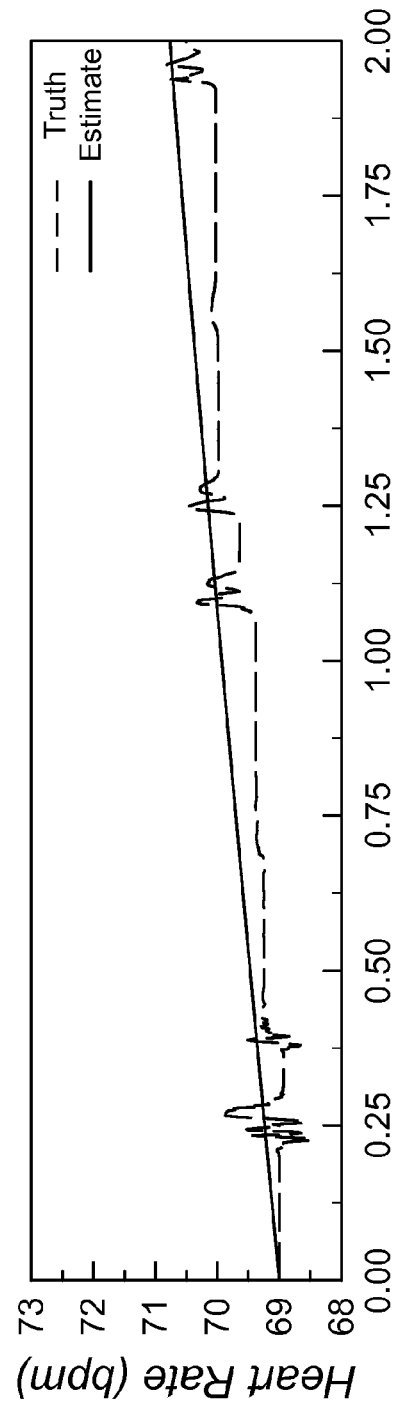

Referring now to FIG. 12A and FIG. 12B, the results of processing a noisy non-stationary ECG signal are shown. Heart rate oscillations representative of normal respiratory sinus arrhythmia are present in the ECG. The processor accomplishes accurate, simultaneous estimation of the true ECG signal and a heart rate that follows closely the true values. Referring now to FIG. 13A and FIG. 13B, the performance of the processor using a noise and artifact-corrupted signal is shown. A clean ECG signal representing one heart beat (truth) was contaminated with additive noise and an artifact in the form of a plateau at R and S peaks (beginning at time=10 sec). Estimates by the processor remain close to the true signal despite the noise and artifact.

The above description describes an apparatus for generation of a physiological estimate of a physiological process of an individual from input data, where the apparatus includes a biomedical instrument, a biomedical device, and/or a biomedical monitoring device having a data processor configured to run a dual estimation algorithm, where the biomedical monitoring device is configured to produce the input data, and where the input data includes at least one of: a photoplethysmogram and an electrocardiogram. The dual estimation algorithm is configured to use a dynamic state-space model to operate on the input data using both an iterative state estimator and an iterative model parameter estimator in generation of the physiological estimate, where the dynamic state-space model is configured to mathematically represent probabilities of physiological processes that generate the physiological estimate and mathematically represent probabilities of physical processes that affect collection of the input data. Generally, the algorithm is implemented using a data processor, such as in a computer, operable in or in conjunction with a biomedical monitoring device.

In yet another embodiment, the method, system, and/or apparatus using a probabilistic model to extract physiological information from a biomedical sensor, described supra, optionally uses a sensor providing time-dependent signals. More particularly, pulse ox and ECG examples were provided, infra, to describe the use of the probabilistic model approach. However, the probabilistic model approach is more widely applicable.

The above description describes an apparatus for generation of a physiological estimate of a physiological process of an individual from input data, where the apparatus includes a biomedical monitoring device having a data processor configured to run a dual estimation algorithm, where the biomedical monitoring device is configured to produce the input data and where the input data includes at least one of: a photoplethysmogram; and an electrocardiogram. The dual estimation algorithm is configured to use a dynamic state-space model to operate on the input data using both an iterative state estimator and an iterative model parameter estimator in generation of the physiological estimate, where the dynamic state-space model is configured to mathematically represent probabilities of physiological processes that generate the physiological estimate and mathematically represent probabilities of physical processes that affect collection of the input data. Generally, the algorithm is implemented using a data processor, such as in a computer, operable in or in conjunction with a biomedical monitoring device.

In yet another embodiment, the method, system, and/or apparatus using a probabilistic model to extract physiological information from a biomedical sensor, described supra, optionally uses a sensor providing time-dependent signals. More particularly, pulse ox and ECG examples were provided, infra, to describe the use of the probabilistic model approach. However, the probabilistic model approach is more widely applicable.

Some examples of physiological sensors used for input into the system with a corresponding physiological model include:
- an ECG having two to twelve leads yielding an ECG waveform used to determine an RR-interval and/or various morphological features related to arrhythmias;
- pulse photoplethysmography yielding a PPG waveform for determination of hemoglobins and/or total hemoglobin;
- capnography or IR absorption yielding a real time waveform for carbon dioxide determination, end-tidal $CO_2$, an inspired minimum, and/or respiration rate;
- a temperature sensor for continuous determination of core body temperature and/or skin temperature;
- an anesthetic gas including nitrous oxide, $N_2O$, and/or carbon dioxide, $CO_2$, used to determine minimum alveolar concentration of an inhaled anesthetic;
- a heart catheter yielding a thermodilution curve for determination of a cardiac index and/or a blood temperature;
- an impedance cardiography sensor yielding a thoracic electrical bioimpedance reading for determination of thoracic fluid content, accelerated cardiac index, stroke volume, cardiac output, and/or systemic vascular resistance;
- a mixed venous oxygen saturation catheter for determination of $SvO_2$;
- an electroencephalogram (EEG) yielding an EEG waveform and characteristics thereof, such as spectral edge frequency, mean dominant frequency, peak power frequency, compressed spectral array analysis, color pattern display, and/or delta-theta-alpha-beta band powers, any of which are used for cardiac functions described herein;
- electromyography (EMG) yielding an EMG waveform including frequency measures, event detection, and/or amplitude of contraction;
- auscultation yielding sound pressure waveforms;
- transcutaneous blood gas sensors for determination of carbon dioxide, $CO_2$, and oxygen, $O_2$;
- a pressure cuff yielding a pressure waveform for determination of systolic pressure, diastolic pressure, mean arterial pressure, heart rate, and/or hemodynamics;
- spirometry combining capnography and flow waveforms for information on respiratory rate, tidal volume, minute volume, positive end-expiratory pressure, peak inspiratory pressure, dynamic compliance, and/or airway resistance;

fetal and/or maternal sensors, such as ECG and sound (auscultatory) sensors for determination of fetal movement, heart rate, uterine activity, and/or maternal ECG;

laser Doppler flowmetry yielding a velocity waveform for capillary blood flow rate;

an ultrasound and/or Doppler ultrasound yielding a waveform, such as a two-dimensional or three-dimensional image, for occlusion of blood vessel walls, blood flow velocity profile, and other body site dependent measures;

a perspirometer yielding a continuous or semi-continuous surface impedance for information on skin perspiration levels; and a digital medical history database to calibrate the model or to screen the database for patient diseases and/or conditions.

Some examples of non-physiological sensors used for input into the system with a corresponding physiological model include:

an accelerometer;
a three axes accelerometer;
a gyroscope;
a compass;
light or a light reading;
a global positioning system, for air pressure data, ambient light, humidity, and/or temperature;
a microphone; and/or
an ambient temperature sensor.

While specific dynamic state-space models and input and output parameters are provided for the purpose of describing the present method, the present invention is not limited to the described dynamic state-space models, sensors, biological monitoring devices, inputs, and/or outputs.

Diagnosis/Prognosis

Figure 14:
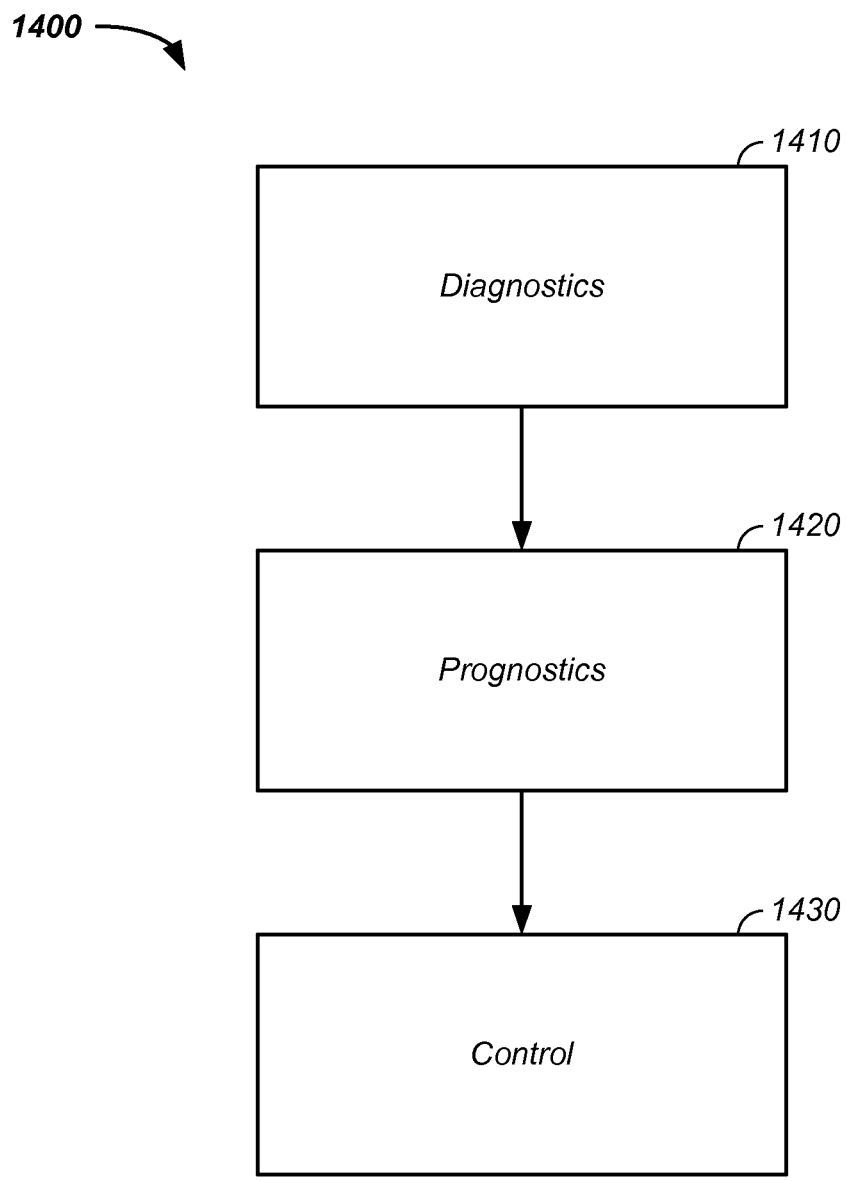
FIG. 14 provides a flowchart of dynamic state-space model diagnostics used as prognosis and control.

Referring now to FIG. 14, the output of the probabilistic digital signal processor 200 optionally is used to diagnose 1410 a system element or component. The diagnosis 1410 is optionally used in a process of prognosis 1420 and/or in control 1430 of the system.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. An apparatus for determination of a left-ventricle stroke volume of a heart of a patient, comprising:
    a medical monitoring device comprising:
        a pulse oximeter;
        a blood pressure meter;
        a non-physiological sensor; and
        a system processor, said system processor configured to process sensor data representing a first physical parameter, said processor comprising:
        a dynamic state-space model, said dynamic state-space model comprising a hemodynamic process model configured to provide a prior probability distribution function using a dual estimation algorithm, said dual estimation algorithm using: (1) input from said pulse oximeter, wherein a blood oxygen saturation and a heart rate are generated using said pulse oximeter; (2) input from said blood pressure meter; and (3) input from said non-physiological sensor, said non-physiological sensor comprising an accelerometer configured to measure state of said pulse oximeter; and
        a probabilistic processor configured to operate on the prior probability distribution function to produce a posterior probability distribution function,
    wherein output correlated with the posterior probability distribution function relates to a second physical parameter, wherein said second physical parameter comprises a physical parameter other than said first physical parameter, wherein said second physical parameter comprises a left ventricle stroke volume of the heart,
    wherein said medical monitoring device outputs the left ventricle stroke volume.

2. The apparatus of claim 1, wherein said second physical parameter further comprises a cardiac output flow rate.

3. The apparatus of claim 1, said medical monitoring device further comprising an auscultation sensor, and said dynamic state-space model further comprising: a hemodynamic dynamic state-space model comprising at least one equation related to blood movement.

4. The apparatus of claim 3, wherein a hemodynamics state parameter input to said hemodynamics dynamic state-space model from said pressure meter comprises an aortic pressure.

5. The apparatus of claim 1, said hemodynamics process model configured to represent state of the patient over time in terms of said second physical parameter; and
    a hemodynamics observation model configured to use a light reading to represent processes involved in collecting the sensor data, wherein said hemodynamics observation model mathematically represents processes involved in use of said biological sensor.

6. The apparatus of claim 5, said hemodynamics process model further comprising:
    a heart model configured to relate cardiac output to heart rate; and
    a vascular model using a time-varying Windkessel compliance function.

7. The apparatus of claim 1, said dynamic state-space model further comprising:
    a physics based probabilistic vascular model configured to represent movement of blood in arteries.

8. The apparatus of claim 1, said medical monitoring device comprising a biomedical monitoring device, wherein the sensor data comprises discrete non-probabilistic input data to said probabilistic processor, said probabilistic processor configured to generate a probabilistic output function.

9. The apparatus of claim 1, said probabilistic processor configured to iteratively circulate a hemodynamics probability distribution function through at least two of:
    said dynamic state-space model;
    a probabilistic updater; and
    a probabilistic sampler.

10. A method for state parameter estimation of a heart of a patient, comprising the steps of:
    providing a biomedical device comprising a first monitoring device and a second monitoring device;
    providing first sensor data representative of a first physical parameter from said first monitoring device, said first monitoring device comprising a pulse oximeter;
    providing second sensor data representative of a second physical parameter from said second monitoring device, said second monitoring device comprising a blood pressure meter;
    processing the sensor data using a computer containing a probabilistic digital signal processor configured to use a dual estimation dynamic state-space model, said dynamic state-space model comprising a hemodynamic process model comprising: (1) a process model receiving first input from said pulse oximeter, wherein a blood oxygen saturation and a heart rate are generated using said pulse oximeter, and input from said blood pressure meter and (2) a noise observation model receiving second input from a non-physiological sensor monitoring physical movement of said first monitoring device;

generating a prior probability distribution function using said dynamic state-space model;

operating on the prior probability distribution function to produce a posterior probability distribution function, wherein output correlated with the posterior probability distribution function relates to a third physical parameter, wherein the third physical parameter comprises a physical parameter other than the first physical parameter, wherein the third physical parameter comprises a physical parameter other than the second physical parameter, wherein said third physical parameter comprises a left ventricle stroke volume of the heart; and outputting said left ventricle stroke volume.

11. The method of claim 10, wherein the first sensor data comprises spectral readings of skin.

12. The method of claim 10, said hemodynamic process model further comprising third sensor data of a fourth physical parameter from a third monitoring device, wherein said third monitoring device comprises an electrocardiogram configured to generate an electrocardiograph, wherein the third sensor data comprises electrical pulse readings through a lung of the patient.

13. The method of claim 10, said step of operating further comprising the steps of:
   using a probabilistic updater to iteratively receive updated sensor data, the sensor data updated in successive iterations of use of said hemodynamics process model; and
   combining the sensor data with input from a medical database of an individual in said dual estimation dynamic state-space model to form a patient specific model.

14. The method of claim 10, further comprising the step of:
   iteratively converting output of said prior probability distribution function using iterative data of the sensor data to generate iterative output of the posterior probability distribution function.

15. The method of claim 10, further comprising the step of:
   processing said prior probability distribution function, wherein said prior probability distribution function comprises a first distribution of a parameter,
   wherein said step of processing generates a second distribution of said parameter, wherein said second distribution comprises a narrower distribution compared to said first distribution.

16. The method of claim 15, wherein said second model parameter distribution comprises a distribution of pressure values.

17. The method of claim 10, said probabilistic digital signal processor further configured with at least one of:
   a light scattering model configured to relate scattered light readings to the left ventricle stroke volume; and
   an absorbance model configured to relate absorbed light readings to the left ventricle stroke volume.

18. The method of claim 10, said dynamic state-space model further comprising:
   using the hemodynamic process model to represent state of a patient over time in terms of state parameters; and
   using the hemodynamic observation model to represent processes involved in collecting the first sensor data.

19. The method of claim 18, said observation model further comprising the step of:
   using a sensor noise model to add noise as a noise probability distribution function to a function representing light values of the sensor data, wherein the added noise comprises movement of sensor noise.

* * * * *